United States Patent
Yano

(10) Patent No.: US 12,048,483 B2
(45) Date of Patent: Jul. 30, 2024

(54) METHOD FOR MANUFACTURING OPTICAL DEVICE, OPTICAL DEVICE, NON-TRANSITORY COMPUTER-READABLE STORAGE MEDIUM, AND COLOR ADJUSTING DEVICE

(71) Applicant: IRIS COMMUNICATION KABUSHIKI KAISHA, Tokyo (JP)

(72) Inventor: Masafumi Yano, Miyagi (JP)

(73) Assignee: IRIS COMMUNICATION KABUSHIKI KAISHA, Tokyo (JP)

(*) Notice: Subject to any disclaimer, the term of this patent is extended or adjusted under 35 U.S.C. 154(b) by 68 days.

(21) Appl. No.: 17/471,310

(22) Filed: Sep. 10, 2021

(65) Prior Publication Data
US 2021/0401284 A1     Dec. 30, 2021

Related U.S. Application Data

(63) Continuation of application No. 16/267,266, filed on Feb. 4, 2019, now Pat. No. 11,141,059, which is a
(Continued)

(30) Foreign Application Priority Data

Aug. 4, 2016 (JP) .................. 2016-153657

(51) Int. Cl.
*A61B 3/02* (2006.01)
*A61B 3/06* (2006.01)
(Continued)

(52) U.S. Cl.
CPC ................ *A61B 3/066* (2013.01); *A61B 3/06* (2013.01); *A61B 3/063* (2013.01); *G02B 5/22* (2013.01); *G02C 7/104* (2013.01)

(58) Field of Classification Search
CPC ........... A61B 3/066; A61B 3/06; A61B 3/063; G02B 5/22; G02C 7/104
(Continued)

(56) References Cited

U.S. PATENT DOCUMENTS 6,851,809 B1 * 2/2005 Sachtler ............... A61B 3/0041
351/242
2006/0256127 A1   11/2006 Cho et al.
(Continued)

FOREIGN PATENT DOCUMENTS

| EP | 1721569 A1 | 11/2006 |
| JP | H06-18819 A | 1/1994 |

(Continued)

OTHER PUBLICATIONS

Aug. 22, 2017 International Search Report issued in International Patent Application No. PCT/JP2017/024643.
(Continued)

*Primary Examiner* — Mahidere S Sahle
(74) *Attorney, Agent, or Firm* — Oliff PLC

(57) ABSTRACT

A method for manufacturing an optical device, includes obtaining a plurality of test images in each of which spectral intensities of a first color component, a second color component and a third color component are separately changeable, changing the spectral intensity of the first color component in at least a first test image, changing the spectral intensity of the second color component in at least a second test image, obtaining a spectral intensity Rs of the first color component and a spectral intensity Gs of the second color component satisfying a particular test condition when a subject is looking at the first and second test images, and manufacturing the optical device including an optical element configured to adjust spectral intensities of the first color component and the second color component, in light
(Continued)

transmitted through the optical element, based on the spectral intensities Rs and Gs.

32 Claims, 9 Drawing Sheets

Related U.S. Application Data continuation-in-part of application No. PCT/JP2017/024643, filed on Jul. 5, 2017.

(51) Int. Cl.
*G02B 5/22* (2006.01)
*G02C 7/10* (2006.01)

(58) Field of Classification Search
USPC ..... 351/242, 159.24, 159.6–159.66; 359/885
See application file for complete search history.

(56) References Cited

U.S. PATENT DOCUMENTS

| | | |
|---|---|---|
| 2007/0236656 A1 | 10/2007 | Jeong et al. |
| 2016/0077361 A1 | 3/2016 | Wold et al. |
| 2021/0076932 A1* | 3/2021 | Nordstrom ............. A61B 3/066 |

FOREIGN PATENT DOCUMENTS

| | | |
|---|---|---|
| JP | 2000-116601 A | 4/2000 |
| JP | 2013-070774 A | 4/2013 |
| WO | 03/084448 A1 | 10/2003 |
| WO | 2005/053521 A1 | 6/2005 |
| WO | 2010111499 A1 | 9/2010 |

OTHER PUBLICATIONS

Mar. 4, 2020 Search Report issued in European Patent Application No. 17836668.8.

* cited by examiner

METHOD FOR MANUFACTURING OPTICAL DEVICE, OPTICAL DEVICE, NON-TRANSITORY COMPUTER-READABLE STORAGE MEDIUM, AND COLOR ADJUSTING DEVICE

CROSS-REFERENCE TO RELATED APPLICATION

This is a continuation of U.S. application Ser. No. 16/267,266 filed on Feb. 4, 2019, which is a Continuation-in-Part of International Application No. PCT/JP2017/024643 filed on Jul. 5, 2017, which claims priority from Japanese Patent Application No. 2016-153657 filed on Aug. 4, 2016. The entire disclosures of the prior applications are incorporated herein by reference in their entirety.

TECHNICAL FIELD

The present disclosure relates to a method for manufacturing an optical device, an optical device, a non-transitory computer-readable storage medium, and a color adjusting device.

BACKGROUND

Color vision deficiency is known as an impairment of a human visual sense. Examples of the color vision deficiency may include color blindness or color weak which is the decreased ability to sense light of a specific wavelength band, and photoallergy from which a sufferer feels dazzled by light. Such color vision deficiency is caused by higher or lower light sensitivity, than that of a healthy person, of three cone cells (i.e., S cone cell, M cone cell and L cone cell) on a retina of a sufferer. The S cone cell, the M cone cell and the L cone cell are sensitive to blue light, green light and red light, respectively. As a method for correcting the color vision deficiency, a method has been known using an optical device (e.g., a color lens) of which the light transmission property is adjusted for the sufferer. Thus, the color vision deficiency may be corrected when the sufferer wears glasses having the color lenses of which the light transmission property is adjusted.

In order to manufacturing a color lens suitable for the sufferer, it is necessary to examine color vision characteristics (sensitivities) of the sufferer to the three lights, i.e., blue light, green light and red light. However, since the number of possible combinations of the sensitivities to the three lights is countless, a large burden for examining the color vision characteristics is imposed on both the examiner and the sufferer to be examined.

Heretofore, methods for manufacturing a color lens suitable for a sufferer have been known. For example, a method has been disclosed for manufacturing glasses depending on which type the color vision characteristics of the sufferer are classified as. In this manufacturing method, the color vision characteristics are classified in 32 types based on results from examining the color vision characteristics of a plurality of sufferers. In the manufacturing method, it is examined which type of the 32 types the color vision characteristics of an individual sufferer are classified as. Thus, the color vision deficiency of the sufferer may be corrected with a color lens having an optical property determined based on the result of the examination.

Further, a method for examining the color vision characteristics has been disclosed. In this examining method, test images for examining the color vision deficiency are displayed on a monitor. A filtering process corresponding to an optical property of a color lens has been applied to each test image. The sufferer selects a specific image that allows the sufferer to easily recognize a character thereon, from among a plurality of test images displayed on the monitor. Thereby, the color vision characteristics of the sufferer may be determined.

Further, another method for examining the color vision characteristics with LEDs ("LED" is an abbreviation of "Light Emitting Diode") has been disclosed. In this examining method, a white LED as a reference light source and a comparative LED configured such that light intensities of Red, Blue and Green lights emitted therefrom are separately changeable are arranged side by side. Based on the light intensities of the Red, Blue and Green lights when the sufferer feels that light emitted from the white LED and light emitted from the comparative LED have the same color, the color vision characteristics of the sufferer may be determined.

SUMMARY OF INVENTION

According to the disclosed methods for examining the color vision characteristics, it is determined which type of the predetermined types the color vision characteristics of the sufferer are classified as. Therefore, if the sufferer has color vision characteristics classified as none of the predetermined types or has color vision characteristics belonging to a middle type between two of the predetermined types, the color vision characteristics of the sufferer might not be examined correctly. Further, according to the other disclosed method for examining the color vision characteristics, it is necessary to change the three intensities of the Red, Blue and Green lights three-dimensionally. Therefore, a period of time for the examination might become so longer that a larger burden of the examination is imposed on the sufferer or a subject to be examined.

According to aspects of the present disclosure, a method for manufacturing an optical device is provided, which includes obtaining a plurality of test images in each of which a spectral intensity of a first color component, a spectral intensity of a second color component, and a spectral intensity of a third color component are separately changeable, a wavelength of the second color component being shorter than a wavelength of the first color component, a wavelength of the third color component being shorter than the wavelength of the second color component, changing the spectral intensity of the first color component without changing the spectral intensity of the third color component, in at least a first test image of the plurality of test images, changing the spectral intensity of the second color component without changing the spectral intensity of the third color component, in at least a second test image, different from the first test image, of the plurality of test images, obtaining a spectral intensity Rs of the first color component in the first test image and a spectral intensity Gs of the second color component in the second test image, the spectral intensity Rs and the spectral intensity Gs satisfying a particular test condition when a subject is looking at the first and second test images, and manufacturing the optical device including an optical element configured to adjust a light intensity of the first color component and a light intensity of the second color component, in light transmitted through the optical element, based on the spectral intensity Rs and the spectral intensity Gs.

According to aspects of the present disclosure, further provided is an optical device that includes an optical element configured to adjust a light intensity of a first color component and a light intensity of a second color component in light transmitted through the optical element, based on a spectral intensity Rs and a spectral intensity Gs, a wavelength of the second color component being shorter than a wavelength of the first color component. The spectral intensity Rs and the spectral intensity Gs are determined by obtaining a plurality of test images in each of which a spectral intensity of the first color component, a spectral intensity of the second color component, and a spectral intensity of a third color component are separately changeable, a wavelength of the third color component being shorter than the wavelength of the second color component, changing the spectral intensity of the first color component without changing the spectral intensity of the third color component, in at least a first test image of the plurality of test images, changing the spectral intensity of the second color component without changing the spectral intensity of the third color component, in at least a second test image, different from the first test image, of the plurality of test images, and obtaining the spectral intensity Rs of the first color component in the first test image and the spectral intensity Gs of the second color component in the second test image, the spectral intensity Rs and the spectral intensity Gs satisfying a particular test condition when a subject is looking at the first and second test images.

According to aspects of the present disclosure, further provided is a non-transitory computer-readable storage medium storing computer-readable instructions configured to, when executed by a computer, cause the computer to obtain a plurality of test images in each of which a spectral intensity of a first color component, a spectral intensity of a second color component, and a spectral intensity of a third color component are separately changeable, a wavelength of the second color component being shorter than a wavelength of the first color component, a wavelength of the third color component being shorter than the wavelength of the second color component, change the spectral intensity of the first color component without changing the spectral intensity of the third color component, in at least a first test image of the plurality of test images, change the spectral intensity of the second color component without changing the spectral intensity of the third color component, in at least a second test image, different from the first test image, of the plurality of test images, change a spectral intensity Rs of the first color component in the first test image and a spectral intensity Gs of the second color component in the second test image, the spectral intensity Rs and the spectral intensity Gs satisfying a particular test condition when a subject is looking at the first and second test images, display an image based on an image signal, and adjust at least one of a spectral intensity of the first color component and a spectral intensity of the second color component, in the image based on the image signal, based on the spectral intensity Rs and the spectral intensity Gs.

According to aspects of the present disclosure, further provided is a color adjusting device including a test image setter configured to obtain a plurality of test images in each of which a spectral intensity of a first color component, a spectral intensity of a second color component, and a spectral intensity of a third color component are separately changeable, a wavelength of the second color component being shorter than a wavelength of the first color component, a wavelength of the third color component being shorter than the wavelength of the second color component, a spectral intensity changer configured to change the spectral intensity of the first color component without changing the spectral intensity of the third color component, in at least a first test image of the plurality of test images, and change the spectral intensity of the second color component without changing the spectral intensity of the third color component, in at least a second test image, different from the first test image, of the plurality of test images, a spectral intensity obtainer configured to obtain a spectral intensity Rs of the first color component in the first test image and a spectral intensity Gs of the second color component in the second test image, the spectral intensity Rs and the spectral intensity Gs satisfying a particular test condition when a subject is looking at the first and second test images, an image displayer configured to display an image based on an image signal, and a spectral intensity adjuster configured to adjust at least one of a spectral intensity of the first color component and a spectral intensity of the second color component, in the image based on the image signal, based on the spectral intensity Rs and the spectral intensity Gs.

BRIEF DESCRIPTION OF THE ACCOMPANYING DRAWINGS

DESCRIPTION OF THE ILLUSTRATIVE EMBODIMENT

It is noted that various connections are set forth between elements in the following description. It is noted that these connections in general and, unless specified otherwise, may be direct or indirect and that this specification is not intended to be limiting in this respect. Aspects of the present disclosure may be implemented on circuits (such as application specific integrated circuits) or in computer software as programs storable on computer-readable media including but not limited to RAMs, ROMs, flash memories, EEPROMs, CD-media, DVD-media, temporary storage, hard disk drives, floppy drives, permanent storage, and the like.

Hereinafter, an illustrative embodiment according to aspects of the present disclosure will be described referring to the accompanying drawings.

[Color Adjusting Device]

Figure 1:
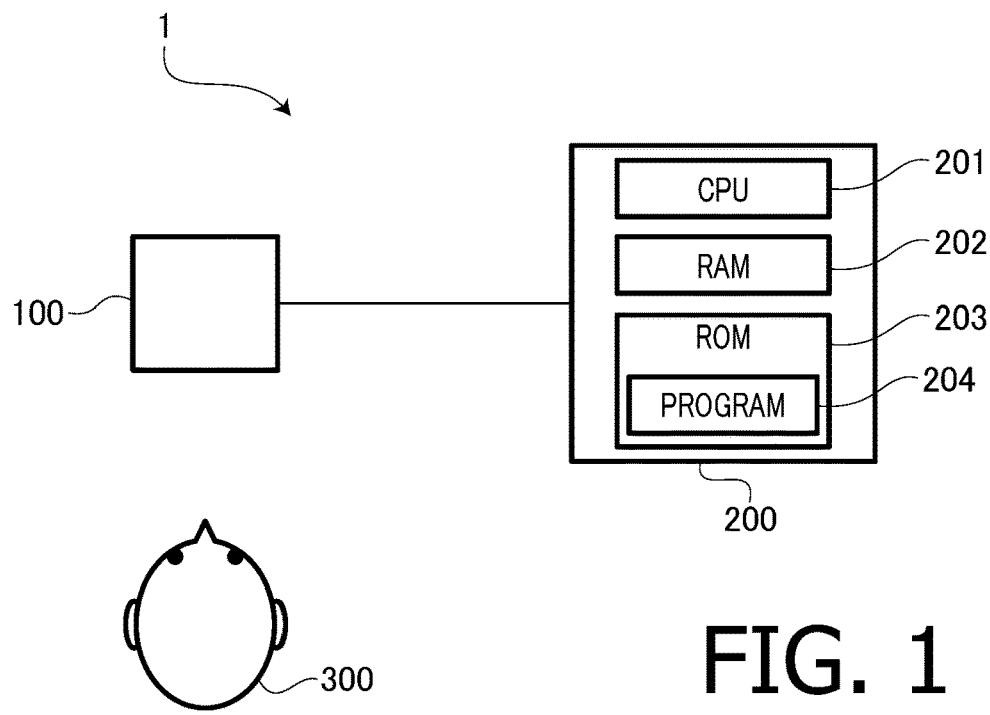
FIG. 1 is a schematic diagram of a color adjusting device in an illustrative embodiment according to aspects of the present disclosure.

FIG. 1 shows a schematic diagram of a color adjusting device 1 configured to execute a color adjusting program in an illustrative embodiment according to aspects of the present disclosure. The color adjusting program is a program for adjusting colors of a screen of a monitor used by a subject 300 in accordance with color vision characteristics of the subject 300. As shown in FIG. 1, the color adjusting device 1 includes a display 100 and a controller 200.

The controller 200 is, for example, an information processing device such as a personal computer or a mobile terminal device. The controller 200 includes a CPU (Central Processing Unit) 201, a RAM (Random Access Memory) 202 and a ROM (Read Only Memory) 203. The CPU 201 is configured to execute a program 204 stored in the ROM 203. The RAM 202 is used as a temporal storage area when the CPU 201 executes the program 204. The program 204 includes an application for adjusting the color adjusting device 1 and an OS (Operating System). The controller 200 is configured to output an image signal to the display 100.

The display 100 is, for example, a liquid crystal display of a CRT (Cathode Ray Tube) display. On the display 100, an image is displayed based on the image signal output from the controller 200.

Figure 2:
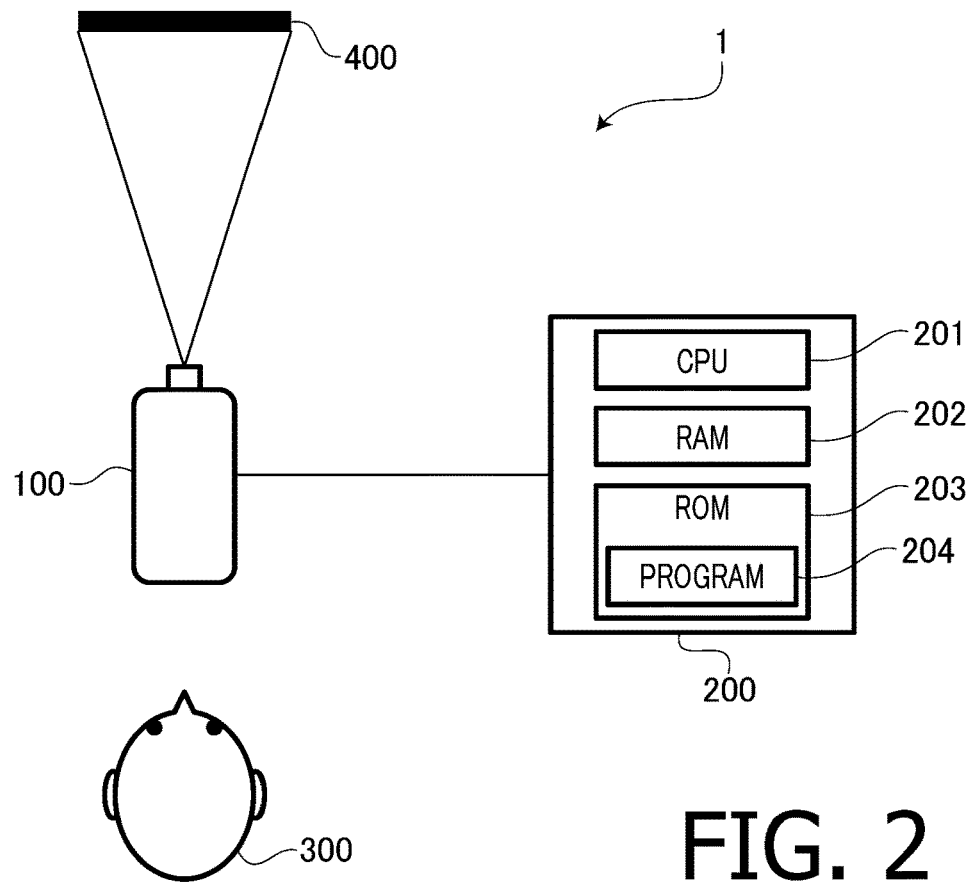
FIG. 2 is a schematic diagram of the color adjusting device in the illustrative embodiment according to aspects of the present disclosure.

The display 100 may be a projector configured to project modulated light. FIG. 2 shows a schematic diagram of the color adjusting device 1 with using a projector 100 as the display 100. With this configuration, the projector projects an image based on the image signal to a screen 400.

[Color Adjusting Method]

Next, a color adjusting method using the color adjusting device 1 will be described.

According to the color adjusting method in the illustrative embodiment, colors of an image displayed on the display 100 are adjusted. A human senses colors by a plurality of cone cells on a retina. The plurality of cone cells include L cone cells, M cone cell and S cone cells. The L cone cells have a relatively high sensitivity to red light compared to a sensitivity to light other than the red light. The M cone cells have a relatively high sensitivity to green light of which wavelength is shorter than that of red light, compared to a sensitivity to light other than the green light. The S cone cells have a relatively high sensitivity to blue light of which wavelength is shorter than that of green light, compared to a sensitivity to light other than the blue light. Wavelength dependency of the sensitivities of the cone cells causes wavelength dependency of color sensitivity of a human. Further, the sensitivity of each of the cone cells has individual difference, and it results in the specific color sensitivity of an individual human.

According to the color adjusting method in the illustrative embodiment, colors of the image displayed on the display 100 are adjusted based on the wavelength dependency or the individual difference of the color sensitivity. Concretely, a spectral intensity of a red color component, a spectral intensity of a green color component and a spectral intensity of a blue color component in the image displayed on the display 100 are adjusted. With this configuration, it is possible to cause the display 100 to display an easily viewable image or an image of which a person can easily identify colors.

Figure 3:
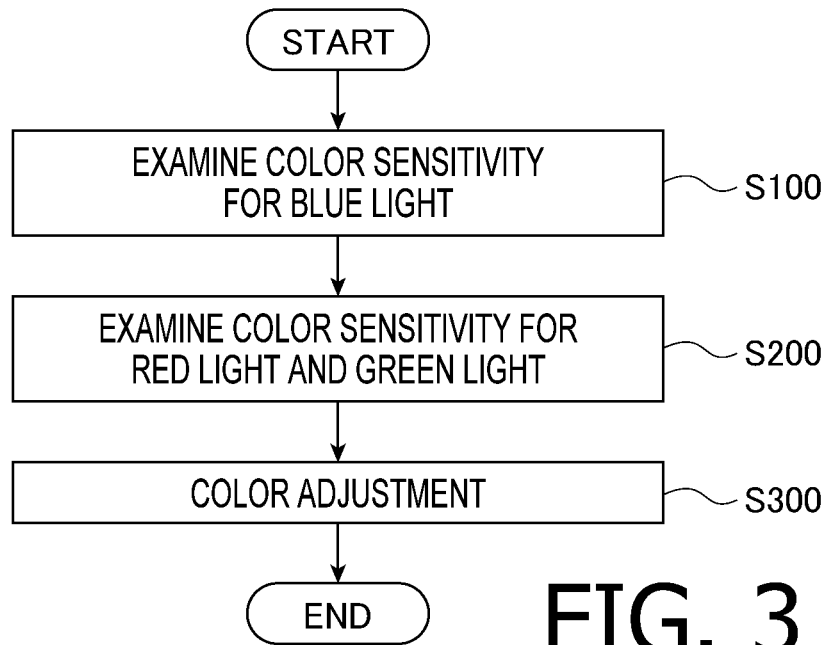
FIG. 3 is a flowchart illustrating the color adjusting method in the illustrative embodiment according to aspects of the present disclosure.

FIG. 3 shows a flowchart illustrating the color adjusting method in the illustrative embodiment. The color adjusting method shown in the flowchart of FIG. 3 is started by the CPU 201 executing the program 204.

In step S100, mainly, the color sensitivity of the subject 300 for blue light is examined. In step S200, the color sensitivities of the subject 300 for red light and green light are examined. In step S300, the colors of the image displayed on a monitor is adjusted based on the color sensitivities of the subject 300. Hereinafter, a detail of each of steps S100, S200 and S300 will be described.

[Step S100]

Figure 4:
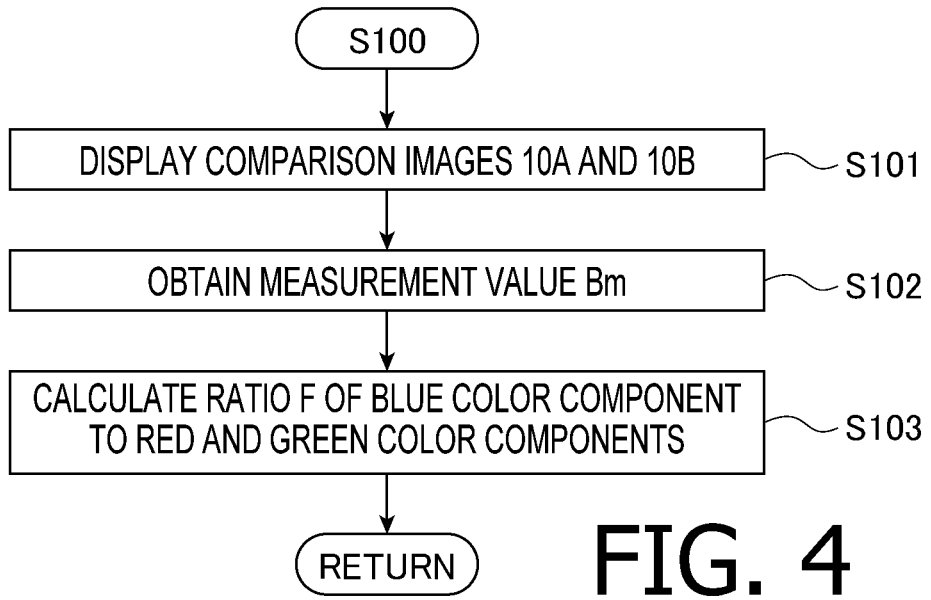
FIG. 4 is a flowchart indicating an examining method of color sensitivity of a subject for blue light in the illustrative embodiment according to aspects of the present disclosure.

FIG. 4 shows a flowchart indicating a detail of step S100. In step S100, the color sensitivity of the subject 300 having photoallergy (or Irlen syndrome) is examined. The Irlen syndrome is thought to be derived from an abnormally high sensitivity of the S cone cells for blue light. In step 100, it is examined that the color sensitivity of the subject 300 for blue light and difference (or ratio) between the color sensitivity for blue light and the color sensitivity for light other than blue light. If the subject does not have the Irlen syndrome, step S100 may be omitted as described later.

[Step S101 of FIG. 4]

Figure 5:
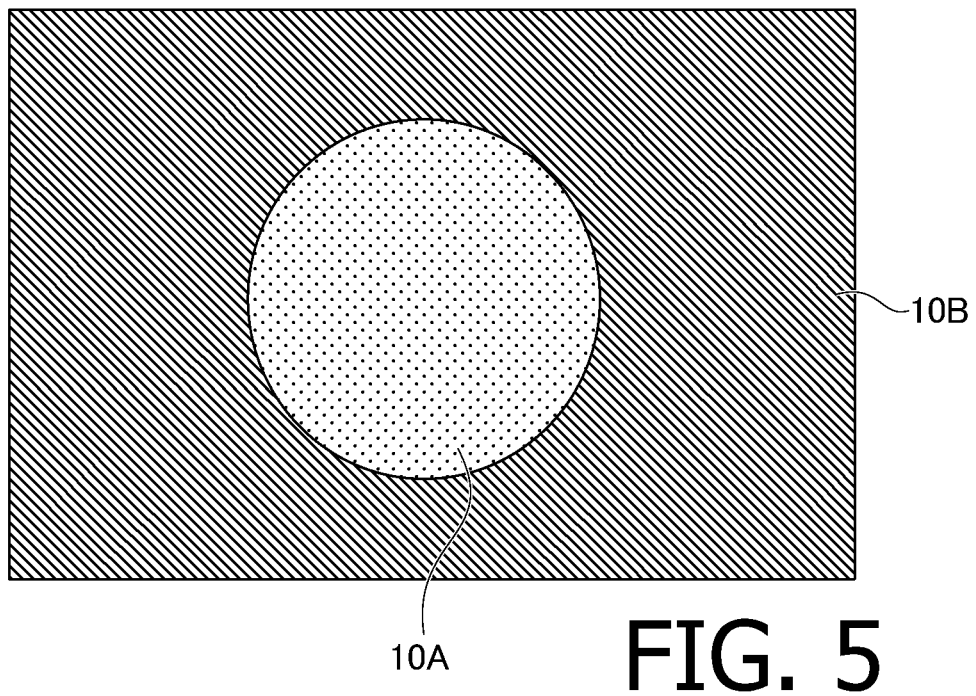
FIG. 5 is an image indicating a comparison image in the illustrative embodiment according to aspects of the present disclosure.

In step S101, two comparison images 10A and 10B are displayed on the display 100. The two comparison images 10A and 10B have different colors from each other. FIG. 5 shows examples of the comparison images 10A and 10B. In the examples, the comparison image 10A having a circular shape is displayed within the comparison image 10B having a rectangular shape. It is noted that the comparison images 10A and 10B may be displayed in proximity to each other such that the comparison images are visibly recognizable, simultaneously. Further, sizes or shapes of the comparison images 10A and 10B are not limited to the example shown in FIG. 5. Specifically, the comparison image 10A may represent a character such as a number or an alphabet, not a circular shape. Both the comparison images 10A and 10B may have rectangular shapes and be displayed side by side.

Colors of each of the comparison images 10A and 10B are represented by color components (R, G, B) in an RGB color space. The "R" indicates a spectral intensity of a red color component in an image, the "G" indicates a spectral intensity of a green color component in an image, and the "B" indicates a spectral intensity of a blue color component in an image. The color components of the comparison image 10A are (R1, 0, B1), and the color components of the comparison image 10B are (0, G1, B1). That is, the blue color component in the comparison image 10A and the blue color component in the comparison image 10B are equal to each other (i.e., the same spectral intensity). Preferably, the red color component R1 in the comparison image 10A is equal to the green color component G1 in the comparison image 10B.

An amplitude of each color component in the comparison images 10A and 10B is individually variable. For example, if the color components in each comparison image are represented by an R image signal, a G image signal and a B image signal of 8-bit (i.e., 256 tones), the amplitude of each color component in the comparison images is variable between 0 and 255.

[Step S102 of FIG. 4]

In step S102, an optimum amplitude of the blue color component for the subject 300 is examined using the comparison images 10A and 10B displayed in step S101. Concretely, in a state where the subject 300 is looking at the comparison images 10A and 10B displayed on the display 100, an examiner simultaneously changes an amplitude of the blue color component B1 in the comparison image 10A and an amplitude of the blue color component B1 in the comparison image 10B in such a manner that the two blue color components B1 in the comparison images 10A and 10B are equal to each other. At the time, the red color component R1 in the comparison image 10A and the green color component G1 in the comparison image 10B are fixed to, for example, about a central value in a variable range (e.g., around 128 in 8-bit). Then, a blue color component Bm, which is a value that causes the subject 300 to visually recognize a color difference between the comparison image 10A and the comparison image 10B most clearly, is measured.

According to a characteristics of the color sensitivity of the subject 300 or a determination criterion of the subject 300 for clarity, a plurality conditions for achieving the highest visibility for the subject 300 to visually recognize the color difference between the comparison image 10A and the comparison image 10B can exist. In such a case, an averaged value or a central value of a plurality of blue color components B1 such that the subject 300 recognizes the color difference most clearly, may be set as the measure value Bm. Or, one of the plurality of blue color components B1 such that the subject 300 recognizes the color difference most clearly may be selected as the measurement value Bm based on liking of the subject 300 (e.g., liking for colors or easiness to see).

For example, if the subject 300 has the Irlen syndrome, when the blue color components B1 in the comparison images 10A and 10B are relatively high, the subject 300 might feel dazzled by the comparison images 10A and 10B, and it is difficult to recognize the color difference between the comparison images 10A and 10B for the subject 300. In that case, the measure value Bm may be smaller than a maximum value Bmax (e.g., 255 in 8-bit) within a settable range of the blue color component.

In contrast, if the subject 300 does not have the Irlen syndrome, even if the blue color components B1 in the comparison images 10A and 10B are relatively high, the subject 300 may not feel dazzled by the comparison images 10A and 10B. Furthermore, as the blue color components B1 in the comparison images 10A and 10B become higher, the subject 300 may feel that each comparison image is bright, and it may be easier to recognize the color difference between the comparison images 10A and 10B. Thus, the measurement value Bm for the subject 300 who does not have the Irlen syndrome is higher than the measurement value Bm for the subject 300 who has the Irlen syndrome.

[Step S103 of FIG. 4]

In step S103, an optimum ratio F of the blue color component to the red and green color components for the subject 300 is examined using the comparison images 10A and 10B. Concretely, in a state where the subject 300 is looking at the comparison images 10A and 10B displayed on the display 100, the examiner changes an amplitude of the red color component R1 in the comparison image 10A and an amplitude of the green color component G1 in the comparison image 10B in such a manner that the red color component R1 and the green color component G1 are equal to each other. At the time, the blue color components B1 in the comparison images 10A and 10B are fixed to the measurement value Bm. It is noted that the red color component R1 in the comparison image 10A and the green color component G1 in the comparison image 10B need not be precisely coincided with each other.

In step S103, an amplitude of the red color component Rc in the comparison image 10A and an amplitude of the green color component Gc in the comparison image 10B, at the time when the subject 300 recognizes the color difference most clearly, are measured. Then, a measurement value Id and the ratio F are calculated in accordance with the following formula 1 and stored in a predetermined memory space (e.g., in the RAM 202) of the controller 200.

$$Id=(Rc+Gc)/2$$

$$F=Id/Bm \quad \text{(Formula 1)}$$

where the measurement value Id is an average of the amplitudes of the red color component Rc and the green color component Gc. It is noted that, since the red color component Rc and the green color component Gc are maintained to have the same value in step S103, one of Rc and Gc may be set as the measurement value Id.

If the subject 300 has the Irlen syndrome, the sensitivity of the subject 300 for red light of green light is lower than that for blue light. In that case, the measurement value Id becomes higher that the measurement value Bm, and the ratio F becomes higher than one.

[Step S200]

Figure 6:
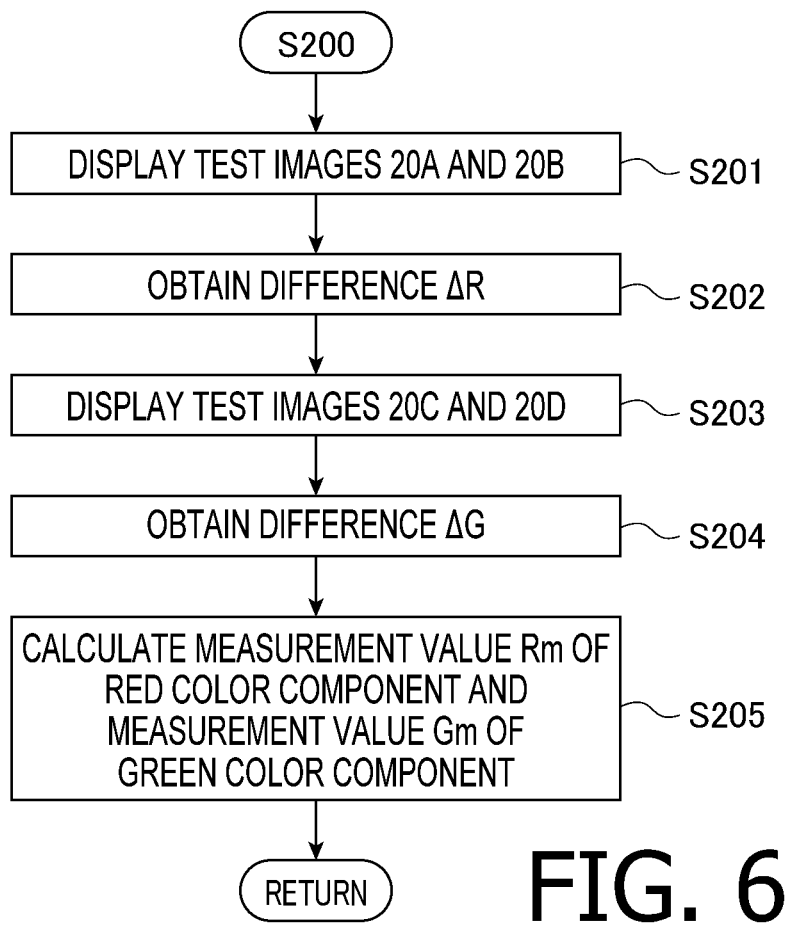
FIG. 6 is a flowchart indicating an examining method of color sensitivities of a subject for red and green light in the illustrative embodiment according to aspects of the present disclosure.

Next, a detail of step S200 will be described. FIG. 6 shows a flowchart illustrating a detail of step S200. In step S200, color sensitivities of the subject 300 for red light and green light are measured.

[Step S201 of FIG. 6]

Figure 7:
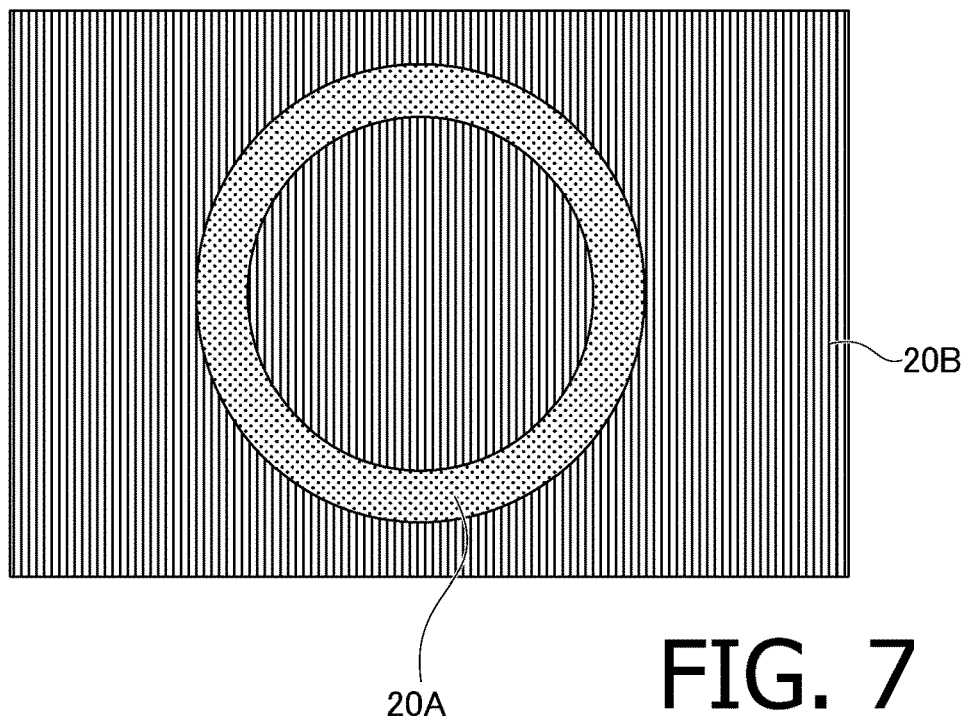
FIG. 7 is an image indicating a test image in the illustrative embodiment according to aspects of the present disclosure.

In step S201, two test images 20A and 20B are displayed on the display 100. FIG. 7 shows examples of the test images 20A and 20B displayed on the display 100. In the examples, the test image 20A having a ring shape is displayed within the test image 20B having a rectangular shape. It is noted that the test images 20A and 20B may be displayed in proximity to each other such that the test images are visibly recognizable, simultaneously. Further, sizes or shapes of the test images 20A and 20B are not limited to the examples shown in FIG. 7. Specifically, the test image 20A may represent a character such as a number or an alphabet, not a ring shape. Both the test images 20A and 20B have rectangular shapes and are displayed side by side.

The color components in the test image 20A are (Rv, G2, B2), and the color components in the test image 20B are (R2, G2, B2). That is, the green and blue color components in the test image 20A are equal to the green and blue color components in the test image 20B, respectively. Further, the red color component R2 and the green color components G2 are equal to each other. The red color component R2 and the green color components G2 may be a central value in a settable range (e.g., around 128 in 8-bit). The red color component R2 and the green color components G2 may be the measurement value Rc and Gc measured in step S103, respectively. Further, the blue color component B2 is measurement value Bm measure in step S102, or zero. It is noted that each of the color components R2, G2 and B2 is not limited to the above value, and may be changed from the above value such that the test images 20A and 20B become easy to see for the subject 300.

[Step S202 of FIG. 6]

In step S202, a color sensitivity of the subject 300 for red light is examined using the test images 20A and 20B display in step S201. Concretely, in a state where the subject 300 is looking at the test images 20A and 20B displayed on the display 100, the examiner changes an amplitude of the red color component Rv in the test image 20A. An initial value of the red color component in the test image 20A is set to R2. Therefore, before the examiner changes an amplitude of the red color component Rv, the test image 20A and the test image 20B have the same color. Then, a red color component Rs1, which is a value that color differences between the test image 20A and the test image 20B is recognizable to the subject 300, is measured. Further, a difference ΔR is calculated in accordance with the following formula 2 and stored in the predetermined memory space.

$$\Delta R = |R2 - Rs1| \quad \text{(Formula 2)}$$

It is noted that, in step S202, the red color component Rv may be changed to a value higher than the initial value R2 or a value lower than the initial value R2. The difference ΔR may be measured in both cases where the red color component is changed to be higher than the initial value and where the red color component is changed to be lower than the initial value. In this case, an average value of two differences ΔR is stored as the difference ΔR.

Further, in step S202, not only the red color component Rv, the red color component R2 and the green color component G2 are changed in such a manner that the red color component R2 and the green color component G2 are equal to each other. In this case, the red color component Rs1, which is an amplitude of the red color component Rv that the color difference between the test image 20A and the test image 20B is recognizable to the subject 300, is measured in each red color component R2 (each green color component G2). Then, the difference ΔR is calculated in each red color component Rs1. A representative value (e.g., an average value, a central value or a most frequent value) of the plurality of the differences ΔR is stored as the difference ΔR.

Figure 8:
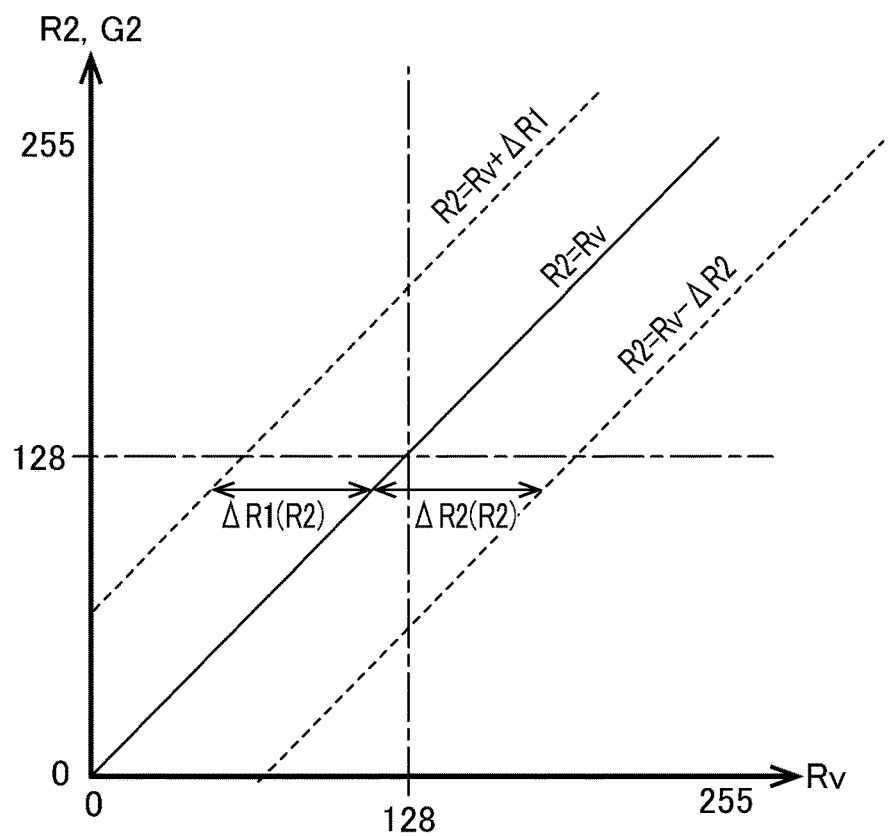
FIG. 8 is a variable area of red color component in a test image in the illustrative embodiment according to aspects of the present disclosure.

FIG. 8 shows an area in which the red color component Rv in the test image 20A and the red color component R2 in the test image 20B can be varied. In FIG. 8, the horizontal axis indicates the red color component Rv in the test image 20A, and the vertical axis indicates the red color component R2 in the test image 20B. Since the red color component R2 in the test image 20A and the green color component G2 in the test image 20B are maintained to have the same value, the vertical axis of FIG. 8 also indicates the green color component G2. In FIG. 8, each color component are represented in 8-bit (i.e., 256 tones).

In FIG. 8, on the straight line of R2=Rv, the test image 20A and the test image 20B have the same color components (R2, G2, B2). Therefore, when R2=Rv, the color difference between the test image 20A and the test image 20B is unrecognizable to the subject 300 regardless of the color vision characteristics thereof.

In step S202, when the red color component Rv in the test image 20A is changed, a coordinate in FIG. 8 is moved in the right and left direction (i.e., along the horizontal axis) from the straight line of R2=Rv. At the time, although the red color component in the test image 20A is changed, none of the color components in the test image 20B is changed. When the color difference between the test image 20A and the test image 20B becomes recognizable to the subject 300, a change amount of the red color component Rv is the difference ΔR. As shown in FIG. 8, the difference ΔR is measured in both sides of the straight line R2=Rv in the right and left direction with respect to each red color component R2 (green color component G2) as the differences ΔR1 and ΔR2, respectively. One of the differences ΔR1 and ΔR2 may be taken as the difference ΔR. Otherwise, an average of the two differences ΔR1 and ΔR2 may be taken as the difference ΔR.

Further, in step S202, the red color component R2 (and the green color component G2) is also changed. Therefore, the difference ΔR(R2) is measured in each red color component R2. Where the difference ΔR(R2) is, for example, an average of the difference ΔR1(R2) and ΔR2(R2) represented in right and left sides of the straight line of R2=Rv. In this case, a representative value of the plurality of differences ΔR(R2) is taken as the difference ΔR.

It is noted that, in step S202, the red color component Rv and the red color component R2 (and the green color component G2) are not necessary to be changed by one tone. For example, it may be changed by several tones such as five tones or ten tones. The red color component R2 is not necessary to be changed in a full range of a variable range (e.g., from 0 to 255 in 8-bit). For example, since brightness of each of the test image 20A and the test image 20B becomes lower as the red color component R2 is changed smaller, there is a possibility that the difference ΔR cannot be measured correctly. Therefore, the red color component R2 may be changed within a range equal to or higher than the initial value (e.g., 128 in 8-bit or Rc). Further, in step S202, the red color component R2 may not be changed and fixed to the initial value.

[Step S203 of FIG. 6]

Figure 9:
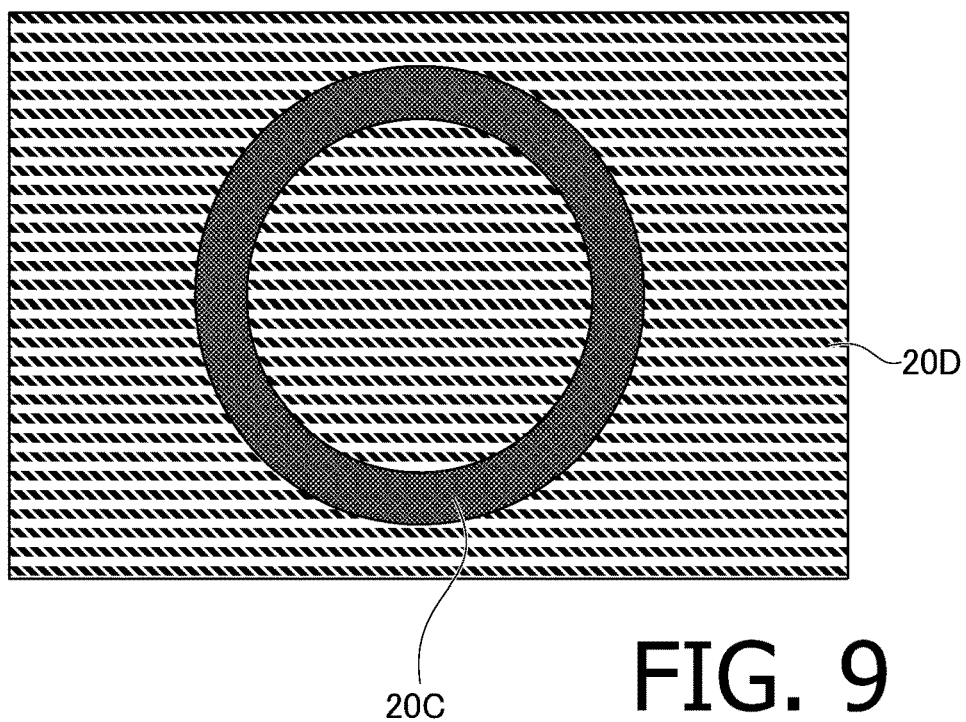
FIG. 9 is an image indicating a test image in the illustrative embodiment of the present disclosure.

In step S203, two test images 20C and 20D are displayed on the display 100. FIG. 9 shows examples of the test images 20C and 20D displayed on the display 100. In the examples, the test image 20C having a circular shape is displayed within the test image 20D having a rectangular shape. It is noted that the test images 20C and 20D may be displayed in proximity to each other such that the test images are visibly recognizable, simultaneously. Further, sizes or shapes of the test images 20C and 20D are not limited to the examples shown in FIG. 9. Specifically, the test image 20C may represent a character such as a number or an alphabet, not a circular shape. Both the test images 20C and 20D have rectangular shapes and are displayed side by side.

The color components in the test image 20C are (R2, Gv, B2), and the color components in the test image 20D are (R2, G2, B2). That is, the red and blue color components in the test image 20C are equal to the red and blue color components in the test image 20D, respectively. Further, the red color component R2 and the green color components G2 are equal to each other. The red color component R2 and the green color components G2 may be a central value in a settable range (e.g., around 128 in 8-bit). The red color component R2 and the green color components G2 may be the measurement value Rc and Gc measured in step S103, respectively. Further, the blue color component B2 is the measurement value Bm measure in step S102, or zero. It is noted that each of the color components R2, G2 and B2 is not limited to the above value, and may be changed from the above value such that the test images 20C and 20D become easy to see for the subject 300.

[Step S204 of FIG. 6]

In step S204, a color sensitivity of the subject 300 for green light is examined using the test images 20C and 20D display in step S203. Concretely, in a state where the subject 300 is looking at the test images 20C and 20D displayed on the display 100, the examiner changes an amplitude of the green color component Gv in the test image 20C. An initial value of the green color component in the test image 20C is set to G2. Therefore, before the examiner changes the amplitude of the green color component Gv, the test image 20C and the test image 20D have the same color. Then, a green color component Gs1, which is a value that color differences between the test image 20C and the test image 20D is recognizable to the subject 300, is measured. Further, a difference ΔG is calculated in accordance with the following formula 3 and stored in the predetermined memory space.

$$\Delta G = |G2 - Gs1| \qquad \text{(Formula 3)}$$

It is noted that, in step S204, the green color component Gv may be changed to a value higher than the initial value G2 or a value lower than the initial value G2. The difference ΔG may be measured in both cases where the green color component is changed to be higher than the initial value and where the green color component is changed to be lower than the initial value. In this case, an average value of two differences ΔG is stored as the difference ΔG.

Further, in step S204, not only the green color component Gv, the red color component R2 and the green color component G2 are changed in such a manner that the red color component R2 and the green color component G2 are equal to each other. In this case, the green color component Gs1, which is an amplitude of the green color component Gv that the color difference between the test image 20C and the test image 20D is recognizable to the subject 300, is measured in each green color component G2 (each red color component R2). Then, the difference ΔG is calculated in each green color component Gs1. A representative value (e.g., an average value, a central value or a most frequent value) of the plurality of the differences ΔG is stored as the difference ΔG.

Figure 10:
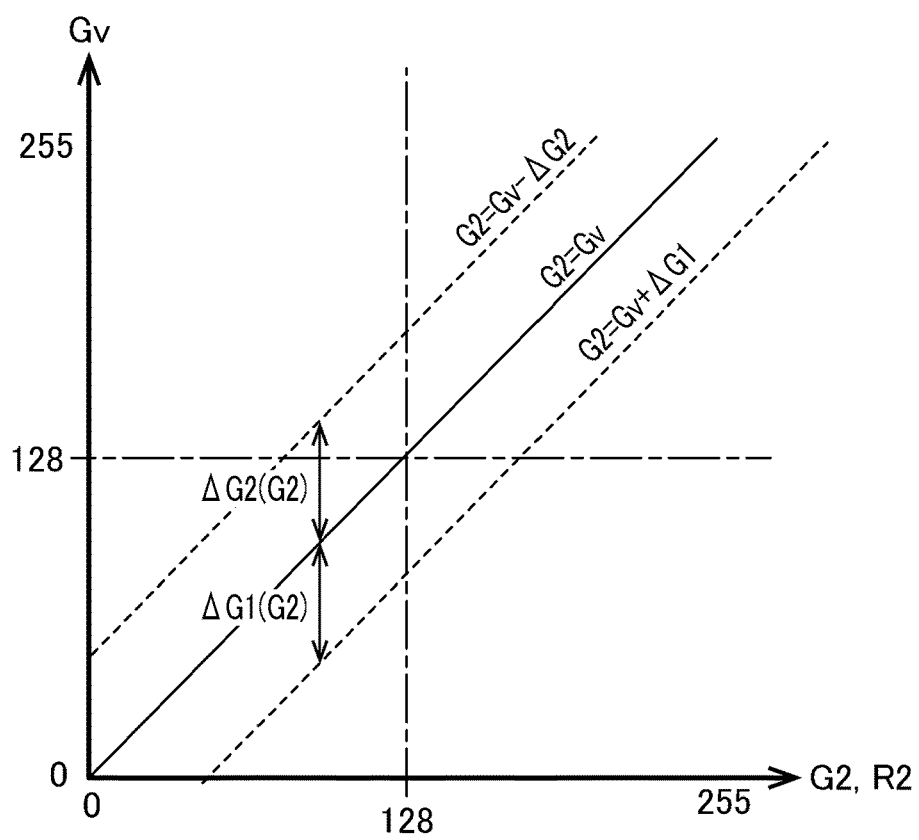
FIG. 10 is a variable area of green color component in a test image in the illustrative embodiment according to aspects of the present disclosure.

FIG. 10 shows an area in which the green color component Gv in the test image 20C and the green color component G2 in the test image 20D can be varied. In FIG. 10, the horizontal axis indicates the green color component Gv in the test image 20C, and the vertical axis indicates the green color component G2 in the test image 20D. Since the green color component G2 in the test image 20C and the red color components R2 in the test image 20C and the test image 20D are maintained to have the same value, the vertical axis of FIG. 10 also indicates the red color component R2. In FIG. 10, each color component are represented in 8-bit (i.e., 256 tones).

In FIG. 10, on the straight line of G2=Gv, the test image 20C and the test image 20D have the same color components (R2, G2, B2). Therefore, when G2=Gv, the color difference between the test image 20C and the test image 20D is unrecognizable regardless of the color vision characteristics of the subject 300.

In step S204, when the green color component Gv in the test image 20C is changed, a coordinate in FIG. 10 is moved in the up and down direction (i.e., along the vertical axis) from the straight line of G2=Gv. At the time, although the green color component in the test image 20C is changed, none of the color components in the test image 20D is changed. When the color difference between the test image 20C and the test image 20D becomes recognizable to the subject 300, a change amount of the green color component Gv is the difference ΔG. As shown in FIG. 10, the difference ΔG is measured in both side of the straight line G2=Gv in the up and down direction with respect to each green color component G2 (each red color component R2) as the differences ΔG1 and ΔG2, respectively. One of the differences ΔG1 and ΔG2 may be taken as the difference ΔG. Otherwise, an average of the two differences ΔG1 and ΔG2 may be taken as the difference ΔG.

Further, in step S204, the green color component G2 (and the red color component R2) is also changed. Therefore, the difference ΔG(G2) is measured in each green color component G2. Where the difference ΔG(G2) is, for example, an average of the difference ΔG1(G2) and ΔG2(G2) represented in up and down sides of the straight line of G2=Gv. In this case, a representative value of the plurality of differences ΔG(G2) is taken as the difference ΔG.

It is noted that, in step S204, the green color component Gv and the green color component G2 (the red color component R2) are not necessary to be changed by one tone. For example, it may be changed by several tones such as five tones or ten tones. The green color component G2 is not necessary to be changed in a full range of a variable range (e.g., from 0 to 255 in 8-bit). For example, the green color component G2 may be changed within a range equal to or higher than the initial value (e.g., 128 in 8-bit or Gc). Further, in step S204, the green color component G2 may not be changed and fixed to the initial value.

[Step S205 of FIG. 6]

In step S205, measurement values Rm and Gm are calculated based on the difference ΔR and the difference ΔG. Concretely, the measurement values Rm and Gm are calculated in accordance with the following formula 4.

$$Rm = \Delta R / \max(\Delta R, \Delta G)$$

$$Gm = \Delta G / \max(\Delta R, \Delta G) \qquad \text{(Formula 4)}$$

where "max (ΔR, ΔG)" means a bigger one of ΔR and ΔG. The calculated measurement values Rm and Gm are stored in the predetermined memory space.

It is noted that the measurement value Rm and the measurement value Gm may be calculated in accordance with the following formula 4A.

$$Rm = C0 \times \Delta R$$

$$Gm = C0 \times \Delta G \qquad \text{(Formula 4A)}$$

where "C0" is constant, and variable according to liking of the subject 300.

The differences ΔR and ΔG measured in steps S202 and S204 correspond to sensitivities of the subject 300 for red light and green light, respectively. In step S202, only the red color component in the test image 20A is change from a state where the test image 20A and the test image 20B have the same colors (a state where the color components in the test image 20A is (R2, G2, B2)). If the sensitivity of the subject 300 for red light is relatively high, even when the red color component in the test image 20A is not changed widely, the subject 300 can recognize the difference between the test image 20A and the test image 20B. In contrast, if the sensitivity of the subject 300 for red light is relatively low, it is difficult for the subject 300 to recognize change of the red color component in the test image 10A. Therefore, until the subject 300 can recognize the difference between the test image 20A and the test image 20B, it is necessary to widely change the red color component in the test image 20A. Thus, the difference ΔR (the measurement value Rm) decreases as the sensitivity of the subject 300 for red light increases, and increases as the sensitivity of the subject 300 for red light decreases.

Similarly to the difference ΔR (the measurement value Rm), the difference ΔG (the measurement value Gm) decreases as the sensitivity of the subject 300 for green light increases, and increases as the sensitivity of the subject 300 for green light decreases. Therefore, ratio between the difference ΔR and the difference ΔG (ration between the measurement value Rm and the measurement value Gm) corresponds to ratio between the sensitivity of the subject 300 for red light and the sensitivity for green light.

[Step S300]

Next, Step S300 will be explained in detail. In step S300, colors of the monitor used by the subject 300 are adjusted based on the measurement value Bm, the maximum value Bmax and the ratio F measured in step S100 and based on the measurement value Rm and Gm measured in step S200. The monitor may be the display 100 of the color adjusting device 1, a monitor of a PC, a mobile terminal or a TV used by the subject 300, or a projector used by the subject 300. Hereinafter, a case where the monitor is the display 100 of the color adjusting device 1 will be explained.

An image (a picture) displayed on the display 100 is generated based on an image signal. For example, RGB image signals respectively representing color components in the RGB color space, or a luminance signal Y and color difference signals Cb and Cr or the like are used as the image signal. Any kind of image signals can be converted to the RGB image signals by applying a matrix conversion process. In step 300, the RGB image signals are adjusted.

Levels Ra, Ga and Ba of the RGB image signals after adjustment of colors can be represented by the following formula 5.

$$Ra = Rd \times F \times Rm$$

$$Ga = Gd \times F \times Gm$$

$$Ba = Bd \times Bm/B\text{max} \quad \text{(Formula 5)}$$

where Rd, Gd and Bd are levels of the RGB image signals before adjustment of the colors.

In the color adjusting process represented by formula 5, the image signal Bd of the blue color component before adjustment is multiplied by a ratio of the measure value Bm to the maximum value Bmax of the blue color component. For example, if the subject 300 has the Irlen syndrome in which the sensitivity for blue light is high, the measurement value Bm is smaller than the maximum value Bmax. Therefore, the level Ba of the adjusted blue color image signal will become smaller than the level Bd of the blue color image signal before adjustment. Thus, it is possible to suppress dazzling that the subject 300 feels with respect to the display.

Further, in the color adjusting process represented by formula 5, the level Rd of the red color image signal before adjustment is multiplied by the ratio F and the measurement value Rm. Additionally, the level Gd of the green color image signal before adjustment is multiplied by the ratio F and the measurement value Gm. The ratio F indicates a ratio of the sensitivities of the subject 300 for red light and green light to the sensitivity for blue light. The measurement values Rm and Gm correspond to the sensitivities of the subject 300 for red light and green light, respectively. Therefore, by this color adjusting process, colors of the image displayed on the display 100 are corrected in accordance with variation of the sensitivities of the subject 300 for red, green and blue lights.

As described above, according to the illustrative embodiment, the levels of the image signals is adjusted in accordance with the color sensitivity of the subject 300, and thereby an image that the subject 300 does not feel dazzled and easily recognizes colors can be displayed on the display 100.

Further, according to the illustrative embodiment, the measurement value Bm, the ratio F, the measurement value Rm and the measurement value Gm are used for the color adjusting process. The measurement value Bm is measured by changing the blue color components in the comparison image 10A and the comparison image 10B one-dimensionally in step S102. Further, the measurement value Rm and Gm are found based on the difference ΔR, which is measured by two-dimensionally changing the red color component Rv and the red color component R2 (and the green color component G2) in step S202, and the difference ΔG, which is measure by two-dimensionally changing the green color component Gv and the green color component G2 (and the red color component R2) in the test image 20C in step S204.

As above, in the illustrative embodiment, any parameter (the measurement value Bm, the ratio F, the measurement value Rm and the measurement valued Gm) used for the color adjusting process is found by changing the color components in the images (the comparison images 10A and 10B, the test images 20A-20D) one-dimensionally or two-dimensionally. Therefore, in comparison to a method that each color component in an image (or an LED light source) is changed three-dimensionally as in the prior arts, it is possible to suppress burdens imposed on the subject 300 and the examiner.

Although the RGB image signals are adjusted by using parameters (i.e., the measurement value Bm, the ratio F, the measurement value Rm and the measurement value Gm) in formula 5, the process of step S300 is not limited to such a process. For example, by applying a matrix conversion to formula 5, it is possible to adjust levels of YCbCr image signals, not the RGB image signals.

Hereinabove, the illustrative embodiment according to aspects of the present disclosure has been described. The present disclosure may be practiced by employing conventional materials, methodology and equipment. Accordingly, the details of such materials, equipment and methodology are not set forth herein in detail. In the previous descriptions, numerous specific details are set forth, such as specific materials, structures, chemicals, processes, etc., in order to provide a thorough understanding of the present disclosure. However, it should be recognized that the present disclosure may be practiced without reapportioning to the details specifically set forth. In other instances, well known processing structures have not been described in detail, in order not to unnecessarily obscure the present disclosure.

Only an exemplary illustrative embodiment of the present disclosure and but a few examples of their versatility are shown and described in the present disclosure. It is to be understood that the present disclosure is capable of use in various other combinations and environments and is capable of changes or modifications within the scope of the inventive concept as expressed herein. For instance, the following modifications according to aspects of the present disclosure are feasible.

(Modification for Test Item)

According to the above described embodiment, although parameters for using the color adjusting process (i.e., the measurement value Bm, the ratio F, the measurement value Rm, and the measurement value Gm) are obtained in step S100 and step S200, the processes of the illustrative embodiment is not limited to such a process.

For example, step 100 may be omitted from the processes indicated in FIG. 3. In that case, the measurement value Bm and the ratio F are not obtained, and the measurement value Rm and the measurement value Gm are obtained. For example, if the subject 300 does not have the Irlen syndrome, the subject 300 might not feel dazzled by a screen displayed on the display. Therefore, with respect to the subject 300 who does not have the Irlen syndrome, measurement of the measurement value B of the blue color component, which is a main cause of feel of dazzling, can be omitted. In that case, the levels Ra, Ga and Ba of the RGB image signals after color adjustment are represented by the following formula 6.

$$Ra = C1 \times Rd \times Rm$$

$$Ga = C1 \times Gd \times Gm$$

$$Ba = C2 \times Bd \quad \text{(Formula 6)}$$

where C1 and C2 are constant values, and can be varied in accordance with liking of the subject 300. For example, both C1 and C2 may be one. Or, if the subject 300 feels dazzled by an image displayed on the display, C2 may be set to be smaller than one.

It is noted that, in step S300, each of the levels Ra, Ga and Ba of the RGB image signals after color adjustment may be calculated based on the following formula 6A.

$$Ra = C1 \times Rd \times Rm/Gm$$

$$Ga = C1 \times Gd$$

$$Ba = C2 \times Bd \quad \text{(Formula 6A)}$$

Further, each of the levels Ra, Ga and Ba of the RGB image signals after color adjustment may be calculated based on the following formula 6B.

$$Ra = C1 \times Rd$$

$$Ga = C1 \times Gd \times Gm/Rm$$

$$Ba = C2 \times Bd \quad \text{(Formula 6B)}$$

The measurement value Rm and the measurement value Gm are varied in accordance with the sensitivity of the subject 300 for the red light and the sensitivity for green light, respectively. In formula 6A or 6B, one of the measurement value Rd and the measurement value Gd is multiplied by ratio between the measurement value Rm and the measurement value Gm. Thus, colors of the image are adjusted based on a difference between the sensitivity of the subject 300 for the red light and the sensitivity for green light. Further, C1 and C2 may be one. If both C1 and C2 are one, only a signal level of the red image signal is adjusted in formula 6A, and only a signal level of the green image signal is adjusted in formula 6B.

Further, step S103 in which the ratio F is measured may be omitted in step S100. In that case, the signal levels Ra, Ga and Ba of the RGB image signals after color adjustment are represented by the following formula 7, respectively.

$$Ra = C3 \times Rd \times Rm$$

$$Ga = C3 \times Gd \times Gm$$

$$Ba = Bd \times Bm/B\text{max} \quad \text{(Formula 7)}$$

where C3 is a constant value, and variable in accordance with liking of the subject 300.

Further, step S200 may not be executed, and only step 100 is executed, and thereby the measurement value Bm and the ratio F may be measured. For example, if the subject 300 has the Irlen syndrome while the ratio of the sensitivity for red light and the sensitivity for green light is the same as that of a person having a normal color sensitivity, step S200 can be omitted. In that case, the signal levels Ra, Ga and Ba of the RGB image signals after color adjustment are represented by the following formula 8.

$$Ra = Rd \times F$$

$$Ga = Gd \times F$$

$$Ba = Bd \times Bm/B\text{max} \quad \text{(Formula 8)}$$

According to the above described embodiment, although step S200 is executed after step S100 is executed, the illustrative embodiment of the present invention is not limited to such a configuration. For example, step S100 may be executed after step S200 has been executed. In that case, the blue color components B2 in the test images 20A-20D used in step S200 is adjusted such that the subject 300 does not feel dazzled by the test images. Further, the blue color components B2 in the test images 20A and 20B may be adjusted such that the subject 300 easily recognize a color difference between the test image 20A and the test image 20B most clearly. The blue color components B2 in the test images 20C and 20D may be adjusted such that the subject 300 easily recognize a color difference between the test image 20C and the test image 20D most clearly. The blue color components B2 in the test images 20A-20D may be set to be zero.

(Modification 1 for Color Adjusting Method)

According to the above described embodiment, the measurement values Rm and Gm are found in step S200. However, a method for finding the measurement values Rm and Gm of the illustrative embodiment is not limited to such a method.

[Step S400]

Figure 11:
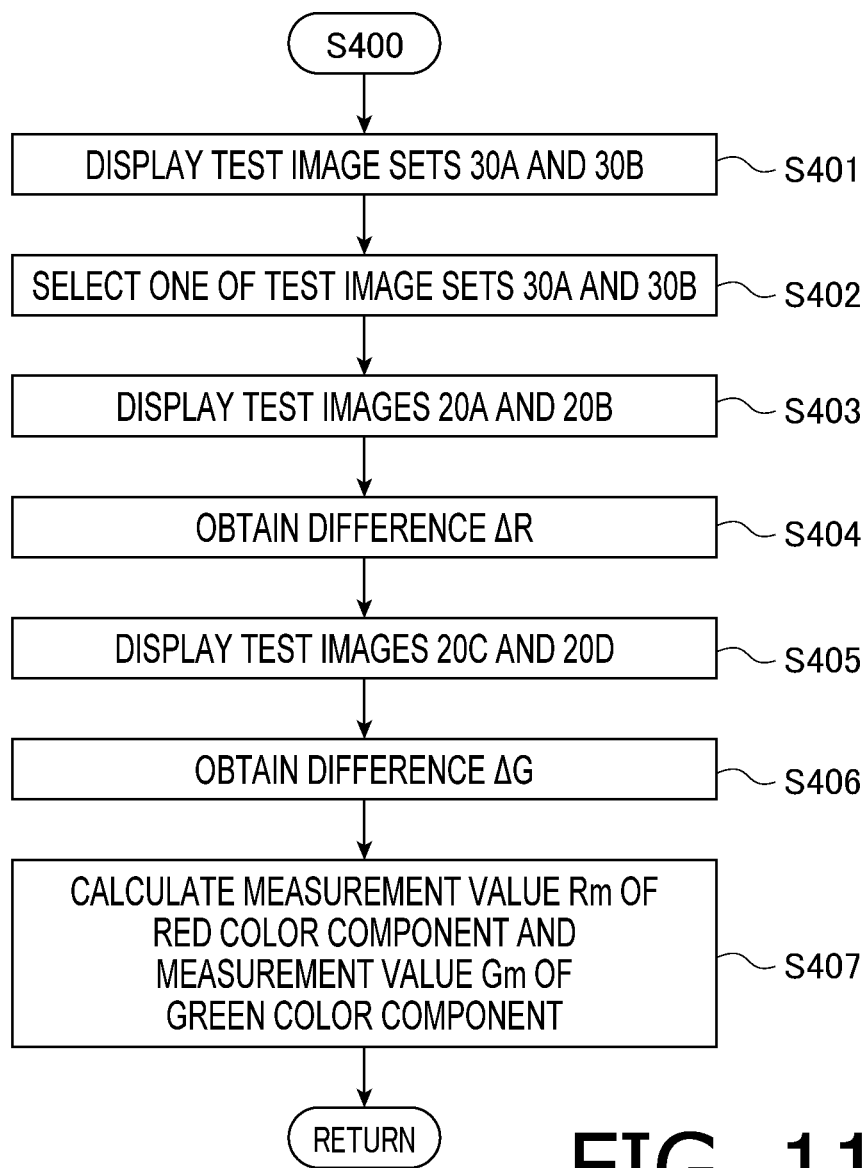
FIG. 11 is a flowchart indicating an examining method of color sensitivities of a subject for red and green light in a modification according to aspects of the present disclosure.

FIG. 11 shows a flowchart illustrating step S400 for finding the measurement values Rm and Gm in the modification 1 of the embodiment. Step S400 is executed instead of step S200 shown in FIG. 3.

[Step S401 of FIG. 11]

Figure 12:
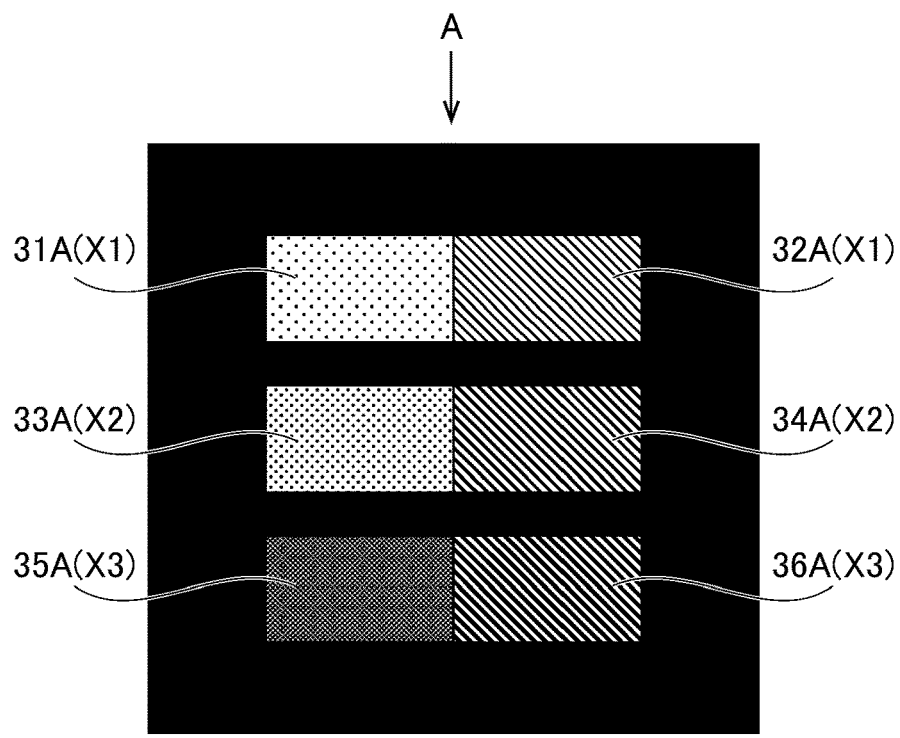
FIG. 12 is an image indicating a test image set in a modification according to aspects of the present disclosure.
Figure 13:
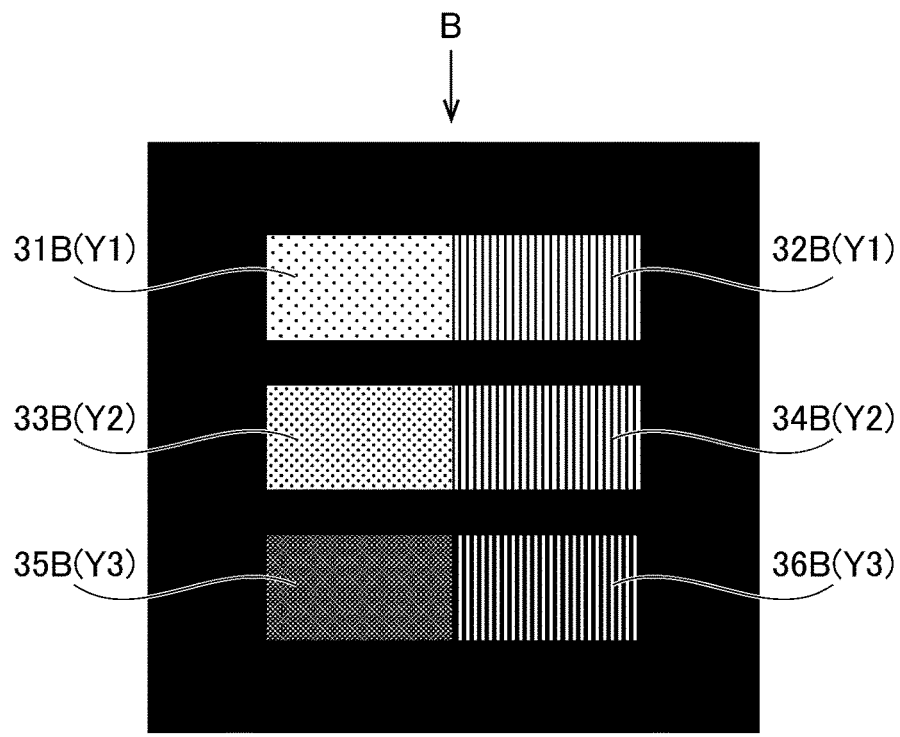
FIG. 13 is an image indicating a test image set in the modification according to aspects of the present disclosure.

In step S401, two test image sets 30A and 30B are displayed on the display, simultaneously or one by one. FIG. 12 is an image indicating the test image set 30A. FIG. 13 is an image indicating the test image set 30B.

The test image set 30A includes three image sets X1, X2 and X3. The image set X1 includes an image 31A and an image 32A. The image set X2 includes an image 33A and an image 33A. The image set X3 includes an image 35A and an image 36A. It is noted that the test image set 30A may include another image set in addition to the image sets X1-X3.

Color components in the test image 31A are (R31x, G31x, B31x), and color components in the test image 31B are (R32x, G31x, B31x). That is, the green color component and the blue color component are equal between the image 31A and the image 32A, respectively. Further, three color components R31x, G31x and B31x have the same value. Therefore, the image 31A is achromatic. The red color component R32x in the image 32A is different from the red color component R31x in the image 31A. Therefore, the image 31A has a red chromatic color when R32x>R31x is satisfied, and has a cyan chromatic color when R32x<R31x is satisfied.

Color components in the test image 33A are (R33x, G33x, B33x), and color components in the test image 34A are (R34x, G33x, B33x). That is, the green color component and the blue color component are equal between the image 33A and the image 34A, respectively. Further, three color components R33x, G33x and B33x have the same value. Therefore, the image 33A is an achromatic image. The red color component R34x of the image 34A is different from the red color component R33x in the image 33A.

Color components in the image 35A are (R35x, G35x, B35x), and color components in the image 36B are (R36x, G35x, B35x). That is, the green color component and the blue color component are equal between the image 35A and the image 36A, respectively. Further, three color components R35x, G35x and B35x have the same value. Therefore, the image 35A is achromatic. The red color component R36x of the image 36A is different from the red color component R35x in the image 35A.

The following table 1 indicates examples of color components in a plurality of the image sets X1-X3 included in the test image set 30A. In each of the image sets, the green color components and the blue color components are equal between the two images, and the red color components have the different values. In each image set, one of the images (the images 31A, 33A and 35A) is achromatic, and the other of the images (the images 32A, 34A and 36A) has a chromatic color.

TABLE 1

|  |  | RED COMPONENT | GREEN COMPONENT | BLUE COMPONENT |
| --- | --- | --- | --- | --- |
| IMAGE SET X1 | IMAGE 31A | 169 | 169 | 169 |
|  | IMAGE 32A | 223 | 169 | 169 |
| IMAGE SET X2 | IMAGE 33A | 128 | 128 | 128 |
|  | IMAGE 34A | 194 | 128 | 128 |
| IMAGE SET X3 | IMAGE 35A | 91 | 91 | 91 |
|  | IMAGE 36A | 128 | 91 | 91 |

The test image set 30B includes three image sets Y1, Y2 and Y3. The image set Y1 includes an image 31B and an image 32B. The image set Y2 includes an image 33B and an image 34B. The image set Y3 an image 35B and an image 36B. It is noted that the test image set 30B may include another image set in addition to the image sets Y1-Y3.

Color components in the test image 31B are (R31y, G31y, B31y), and color components in the test image 32B are (R31y, G32y, B31y). That is, the red color component and the blue color component are equal between the image 31B and the image 32B, respectively. Further, three color components R31y, G31y and B31y have the same value. Therefore, the image 31B is an achromatic image. The green color component G32y of the image 32B is different from the green color component G31y of the image 31B. Therefore, the image 31B has a green chromatic color when G32y>G31y is satisfied, and has a magenta chromatic color when G32y<G31y is satisfied.

Color components in the test image 33B are (R33y, G33y, B33y), and color components in the test image 34B are (R33y, G34y, B33y). That is, the red color component and the blue color component are equal between the image 33B and the image 34B, respectively. Further, three color components R33y, G33y and B33y have the same value. Therefore, the image 33B is achromatic. The green color component G34y of the image 34B is different from the green color component G33y of the image 33B.

Color components in the image 35B are (R35y, G35y, B35y), and color components in the image 36B are (R35y, G36y, B35y). That is, the red color component and the blue color component are equal between the image 35B and the image 36B, respectively. Further, three color components R35y, G35y and B35y have the same value. Therefore, the image 35B is achromatic. The green color component G36y in the image 36B is different from the green color component G35y in the image 35B.

The following table 2 indicates examples of color components in a plurality of the image sets Y1-Y3 included in the test image set 30B. In each of the image sets, the red color components and the blue color components have the same value between the two images, and the green color components have the different values. In each image set, one of the images (the images 31B, 33B and 35B) is achromatic, and the other of the images (the images 32B, 34B and 36B) has a chromatic color.

TABLE 2

|  |  | RED COMPONENT | GREEN COMPONENT | BLUE COMPONENT |
| --- | --- | --- | --- | --- |
| IMAGE SET Y1 | IMAGE 31B | 169 | 169 | 169 |
|  | IMAGE 32B | 169 | 223 | 169 |
| IMAGE SET Y2 | IMAGE 33B | 128 | 128 | 128 |
|  | IMAGE 34B | 128 | 194 | 128 |
| IMAGE SET Y3 | IMAGE 35B | 91 | 91 | 91 |
|  | IMAGE 36B | 91 | 128 | 91 |

[Step S402 of FIG. 11]

In step S402, the color sensitivity of the subject 300 is examined by using the test image sets 30A and 30B displayed in step S401. Concretely, the subject 300 watches the test image sets 30A and 30B and selects one of the test image sets of which the difference between the two images included in each of the image sets is easily recognizable. When the subject 300 selects one of the test image sets 30A and 30B, information indicating the selection is stored in the predetermined memory space.

As an example, a case where the sensitivity of the subject 300 for red light is higher than the sensitivity for green light will be explained. In that case, the subject 300 can easily recognize variation of the red color component compared with variation of the green color component in an image. Therefore, the subject 300 feels that the test image set 30A is easier to identify the difference of two images included in each image set. Thus, if the subject 300 feels that the test image set 30A is easier to identify the difference of two images included in each image set, the sensitivity of the subject 300 for red light is supposed to be higher than the sensitivity for green light. In contrast, if the subject 300 feels that the test image set 30B is easier to identify the difference of two images included in each image set, the sensitivity of the subject 300 for green light is supposed to be higher than the sensitivity for red light.

[Step S403 of FIG. 11]

In step S403, the same process as step S201 is executed. That is, in step S403, two test images 20A and 20B are displayed on the display 100. The color components in the test image 20A are (Rv, G2, B2), and the color components in the test image 20B are (R2, G2, B2).

[Step S404 of FIG. 11]

Step S404 is the same as step S202 except that variation ranges of the red color component Rv, and the red color component R2 and the green color component G2 are different. The variation ranges of the red color component Rv, and the red color component R2 and the green color component G2 in step S404 depend on the selection of the subject 300 in step S402.

In step S402, if the subject 300 feels that the test image set 30A is easier to identify the difference of two images included in each image set, the sensitivity of the subject 300 for red light is supposed to be higher than the sensitivity for green light. Therefore, by using test images having the green color component higher than the red color component, it is possible to execute a test of the color sensitivity in a state where the difference between the sensitivity of the subject 300 for red light and the sensitivity for green light is suppressed. In that case, in step S404, the red color component Rv, and the red color component R2 and the green color component G2 are varied within a range satisfying Rv≤G2. This range corresponds to an area on a left side (or an upside) of the straight line of R2=Rv in FIG. 8.

On the other hand, in step S402, if the subject 300 feels that the test image set 30B is easier to identify the difference of two images included in each image set, the sensitivity of the subject 300 for green light is supposed to be higher than the sensitivity for red light. Therefore, by using test images having the red color component higher than the red color component, it is possible to execute a test of the color sensitivity in a state where the difference between the sensitivity of the subject 300 for red light and the sensitivity for green light is suppressed. In that case, in step S404, the red color component Rv, and the red color component R2 and the green color component G2 are varied within a range satisfying Rv≥G2. This range corresponds to an area on a right side (or a downside) of the straight line of R2=Rv in FIG. 8.

In step S404, the red color component Rv, and the red color component R2 and the green color component G2 are varied, and an amplitude Rs1 of the red color component Rv in the test image 20A is measured. The amplitude Rs1 is an amplitude that the color difference between the test image 20A and the test image 20B is recognizable to the subject 300. Further, the difference ΔR is calculated in accordance with formula 2 and stored in the predetermined memory space.

[Step S405 of FIG. 11]

In step S405, the same process as step S203 is executed. That is, in step S405, two test images 20C and 20D are displayed on the display 100. The color components in the test image 20C are (R2, Gv, B2), and the color components in the test image 20D are (R2, G2, B2).

[Step S406 of FIG. 11]

Step S406 is the same as step S204 except that variation ranges of the green color component Gv, and the red color component R2 and the green color component G2 are different. The variation ranges of the green color component Gv, and the red color component R2 and the green color component G2 in step S406 depend on the selection of the subject 300 in step S402.

In step S402, if the subject 300 feels that the test image set 30A is easier to identify the difference of two images included in each image set, the green color component Gv, and the red color component R2 and the green color component G2 are varied within a range satisfying R2≤Gv in step S406. The range corresponds to an area on a left side (or an upside) of the straight line of G2=Gv in FIG. 10. In contrast, in step S402, if the subject 300 feels that the test image set 30B is easier to identify the difference of two images included in each image set, the green color component Gv, and the red color component R2 and the green color component G2 are varied within a range satisfying R2≥Gv in step S406. The range corresponds to an area on a right side (or a downside) of the straight line of G2=Gv in FIG. 10.

In step S406, the green color component Gv, and the red color component R2 and the green color component G2 are varied, and an amplitude Gs1 of the green color component Gv in the test image 20C is measured. The amplitude Gs1 is an amplitude that the color difference between the test image 20C and the test image 20D is recognizable to the subject 300. Further, the difference ΔG is calculated in accordance with formula 3 and stored.

[Step S407 of FIG. 11]

In step S407, the same process as the process of step S205 is executed. That is, in step S407, the measurement values Rm and Gm are calculated and stored.

As described above, according to the modification 1, is step S402, it is measured which of the sensitivity of the subject 300 for red light and the sensitivity for green light is higher. Then, when the differences ΔR and ΔG are measured, variation ranges of the color components in the test images is restricted in accordance with the sensitivities of the subject 300. Therefore, it is possible to further suppress burdens, for measuring the measurement value Rm and Gm, imposed on the subject 300 and the examiner.

(Modification 2 for Color Adjusting Method)

A method for finding the measurement values Rm and Gm in the illustrative embodiment is not limited to the method described in step s200 or step S400.

Figure 14:
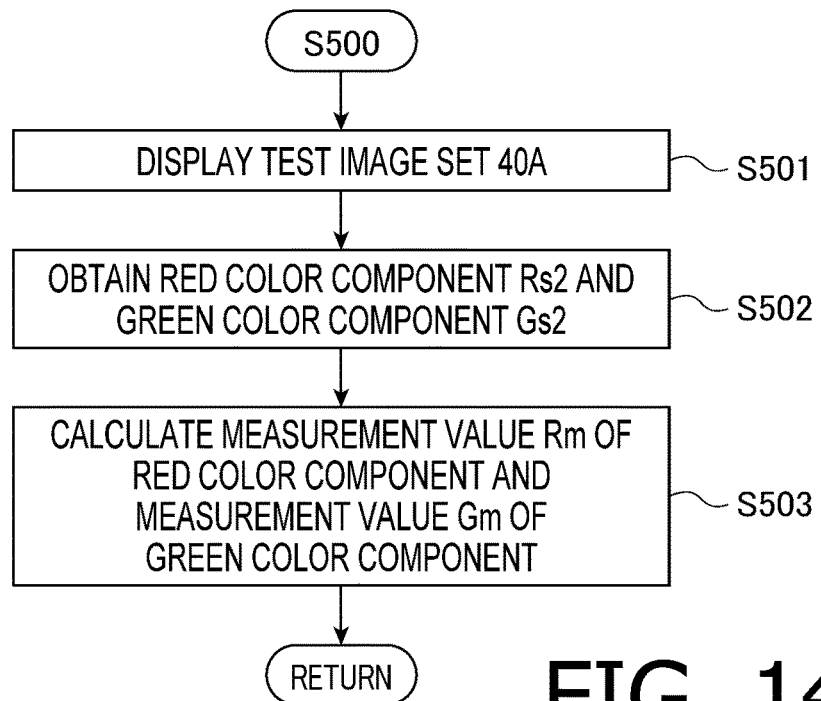
FIG. 14 is a flowchart indicating an examining method of color sensitivities of a subject for red and green light according to a modification of an embodiment of the present disclosures.

FIG. 14 shows a flowchart illustrating step S500 for finding the measurement values Rm and Gm in the modification 2 of the illustrative embodiment. Step S500 is executed instead of step S200 shown in FIG. 3.

[Step S501 of FIG. 14]

Figure 15:
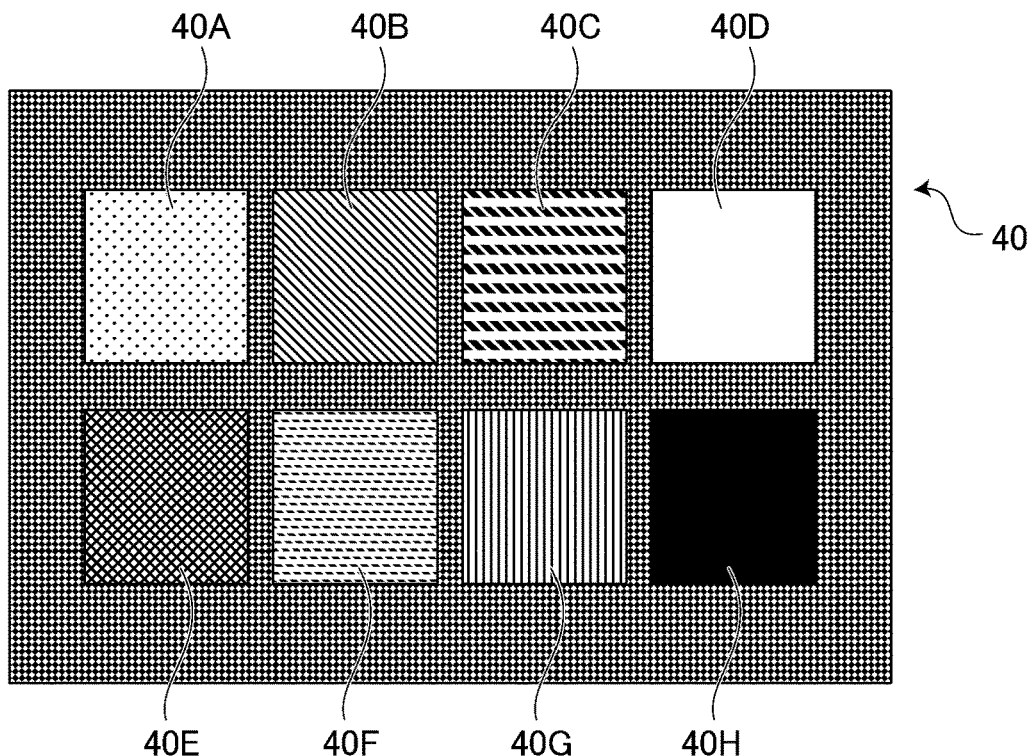
FIG. 15 is an image indicating a test image set in the modification according to aspects of the present disclosure.

In step S501, the test image set 40 is displayed on the display 100. FIG. 15 shows the test image set 40. As shown in FIG. 15, the test image set 40 includes eight test images 40A-40H. The following table 3 indicates color components of each test image 40A-40H.

TABLE 3

|  | RED COMPONENT | GREEN COMPONENT | BLUE COMPONENT |
| --- | --- | --- | --- |
| TEST IMAGE 40A | R4 | 0 | 0 |
| TEST IMAGE 40B | 0 | G4 | 0 |
| TEST IMAGE 40C | 0 | 0 | B4 |
| TEST IMAGE 40D | R4 | G4 | B4 |
| TEST IMAGE 40E | R4 | G4 | 0 |
| TEST IMAGE 40F | 0 | G4 | B4 |
| TEST IMAGE 40G | R4 | 0 | B4 |
| TEST IMAGE 40H | 0 | 0 | 0 |

The test images 40A, 40D, 40E and 40G have the same red color components R4. The test images 40B, 40D, 40E and 40F have the same green color components G4. The red color component R4 and the green color component G4 are individually variable in all the test images 40A-40H. For example, if the red color component R4 is varied, red color components in all the images 40A-40l1 are varied at the same rate. However, since the test images 40B, 40C, 40F and 40H do not have the red color component (i.e., an amplitude of the red color component is zero), the red color components in the test images 40B, 40C, 40F and 40H are not variable. Further, if the green color component G4 is varied, green color components in all the images 40A-40H are varied at the same rate. However, since the test images 40A, 40C, 40G and 40H do not have the green color component (i.e., an amplitude of the green color component is zero), the green color components in the test images 40A, 40C, 40G and 40H are not variable.

Further, the test images 40C, 40D, 40F and 40G have the same blue color component B4. The blue color component B4 is set to the measurement value Bm. As explained in the above "Modification for test item," step S100 may be omitted before execution of step S500. In that case, since the measurement value Bm has not been measured, the blue color component B4 is set such that the subject 300 does not feel dazzled by the test image set 40.

[Step S502 of FIG. 14]

In step S502, the color sensitivities of the subject 300 are examined by using the test image set 40. Concretely, in a state where the subject 300 is looking at the test image set 40 displayed on the display 100, the examiner separately changes amplitudes of the red color components R4 and the green color components G4 in the test image images 40A-40H. Then, a red color component Rs2 and a green color component Gs2, which are values that cause the subject 300 to recognize color differences among the eight test images 40A-40H most clearly, are measured.

In step S502, according to characteristics of the color sensitivity of the subject 300 or a determination criterion of the subject 300 for clarity, there might exist a plurality conditions that the subject 300 can recognize color differences to the test images 40A-40H most clearly. Therefore, if there exists a plurality of red color components R4 such that the subject 300 can recognize most clearly, a central value of the plurality of red color components R4 may be set as the red color component Rs2. Further, if there exists a plurality of green color components G4 such that the subject 300 can recognize most clearly, a central value of the plurality of green color components G4 may be set as the green color component Gs2. Or, the red color components R4 and the green color component G4 in one of the plurality of conditions that the subject 300 recognizes the color difference of the test images 40A-40H most clearly may be set as the red color component Rs2 and the green color component Gs2, respectively, based on liking of the subject 300 (e.g., liking for colors or easiness to see).

[Step S503 of FIG. 14]

In step S503, the measurement values Rm and Gm are measured based on the red color component Rs2 and the green color component Gs2. Specifically, the measurement values Rm and Gm are calculated in accordance with the following formula 9.

$$Rm = Rs2/\max(Rs2, Gs2)$$

$$Gm = Gs2/\max(Rs2, Gs2) \quad \text{(Formula 9)}$$

The calculated measurement values Rm and Gm are stored in the predetermined memory space.

The test image set 40 used in step S502 may include a plurality of test images having various colors, and the number of the test images is not limited to eight.

Further, the color components in the test images 40A-40H included in the test image set are not limited to examples indicated in table 3. For example, the test images 40A, 40D, 40E and 40G do not necessary to have the same red color component, and the red color components may different between the test images. Further, the test images 40B, 40D, 40E and 40F do not necessary to have the same green color component, and the green color components may different between the test images. In that case, the examiner adjusts the red color component in each of the test images 40A-40H at the same rate and adjusts the green color component in each of the test images 40A-40H at the same rate in step S502. Further, the red color component Rs2 and the green color component Gs2 in this case are the maximum value of the red color component and the maximum value of the green color component in the plurality of test images 40A-40H, respectively, on a condition that the subject 300 can clearly recognize the color differences of the eight test images 40A-40H.

It is noted that an image representing landscape pictures, paintings, still-life painting or the like including various colors may be used for the test instead of the test image set 40. In that case, each of RGB color components in whole of the image used for the test is separately changeable by the controller 200.

It is noted that, although the red color component R4 and the green color component G4 are changed two-dimensionally in step S502, step S502 of the modification is not limited to such a process. For example, instead of step S502, the following steps S502A and S502B may be executed.

[Step S502A]

In step S502A, in a state where the subject 300 is looking at the test image set 40 displayed on the display 100, the examiner changes only the red color component R4 while fixing the green color component G4 in the test images 40A-40H. At the time, the green color component G4 is fixed to the measurement value Gc measured in step S103. If step S502A is executed without executing step S103, for example, the green color component G4 is set to the maximum value (e.g., 255 in 8-bit) of settable values. Then, the red color component Rs2, which is a value that the subject 300 can recognize color differences of the eight test images 40A-40H most clearly, is measured.

[Step S502B]

In step S502B, in a state where the subject 300 is looking at the test image set 40 displayed on the display 100, the examiner changes only the green color component G4 while fixing the red color component R4 in the test images 40A-40H. At the time, the red color component R4 is fixed to the measurement value Rc measured in step S103. If step S502B is executed without executing step S103, for example, the red color component R4 is set to the maximum value (e.g., 255 in 8-bit) of settable values. Then, the green color component Gs2, which is a value that the subject 300 can recognize color differences of the eight test images 40A-40H most clearly, is measured.

As described above, in steps S502A and S502B, while one of the red color component R4 and the green color component G4 is fixed, the other is change one-dimensionally. Therefore, test conditions in steps S502A and S502B are less than step S502 in which the red color component R4 and the green color component G4 are changed two-dimensionally, and thereby it is possible to suppress burdens for the test imposed on the subject 300 and the examiner.

(Modification for Color Adjustment)

In step S300 in the above described embodiment, the levels of the image signals of the monitor are adjusted. However, step S300 in the embodiment is not limited to such a process. For example, in step S300, by using each parameter (the measurement value Bm, the ratio F, the measure value Rm and the measurement value Gm), an optical device adjusting the color sensitivity of the subject 300 may be manufactured. The optical device may be mounted on eyes of the subject 300 as eyeglasses or a contact lens.

When transmittance for light of a red wavelength band is TR, transmittance for light of a green wavelength band is TG and transmittance for light of a blue wavelength band is TB, the optical device is designed such that the ratio indicated by the following formula 10 is satisfied.

$$TR:TG:TB = F \times Rm : F \times Gm : Bm/B\max \qquad \text{(Formula 10)}$$

where TR is transmittance in a wavelength band around 700 nm, TG is transmittance in a wavelength band around 546.1 nm and TB is transmittance in a wavelength band around 435.8 nm.

When the optical device is designed, a border between the red wavelength band and the green wavelength band and a border between the green wavelength band and the blue wavelength band are not limited to particular wavelength. For example, when the optical device is designed, the border between the red wavelength band and the green wavelength band may be a wavelength between 700 nm and 546.1 nm. Further, when the optical device is designed, the border between the green wavelength band and the blue wavelength band may be a wavelength between 546.1 nm and 435.8 nm. Additionally, transmittance of the optical device may be designed such that the transmittance is gradually changed between the red wavelength band and the green wavelength band and between the green wavelength band and the blue wavelength band. The optical device may be anything as long as the formula 10 is satisfied, and a material thereof or a principle of changing a transmission spectrum is not limited to a particular kind.

Figure 16:
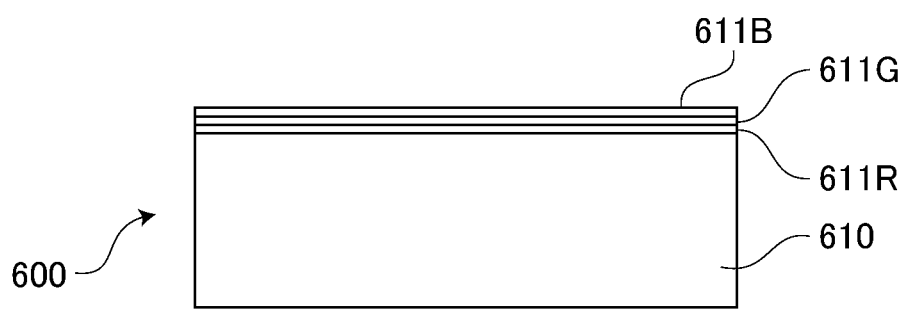
FIG. 16 is a cross-section view of an optical device in the illustrative embodiment according to aspects of the present disclosure.

For example, the optical device may be manufactured by applying color coating to a transparent substrate such as eyeglasses or a contact lens. FIG. 16 shows a cross-section view of an optical device 600 with color coating. A material of the transparent substrate 610 may a material through which a visible light is transmitted without attenuating, and glass or resin may be used. On a surface of the substrate 610, color coating 611R having transmittance TR for light of a red wavelength band, color coating 611G having transmittance TG for light of a green wavelength band and color coating 611B having transmittance TB for light of a blue wavelength band are applied.

Degree (e.g., thickness of coating) of each of the color coating 611R, the color coating 611G and the color coating 611B is determined such that transmittance of the optical device 600 satisfies formula 10. Each of the color coating 611R, the color coating 611G and the color coating 611B may be a dielectric multilayer film coated on the transparent material. Further, Each of the color coating 611R, the color coating 611G and the color coating 611B may be applied by immersing the substrate 610 into stain solution in which a stain is dissolved. The color coating 611R, the color coating 611G and the color coating 611B need not be coated separately. For example, single color coating may change transmission spectrums of all of red, green and blue wave length bands.

Further, the color coating 611R may relatively change an intensity of light of the red wavelength band by changing transmittance of light other than the red wavelength band. The color coating 611G may relatively change an intensity of light of the green wavelength band by changing transmittance of light other than the green wavelength band. The color coating 611B may relatively change an intensity of light of the blue wavelength band by changing transmittance of light other than the blue wavelength band.

Figure 17:
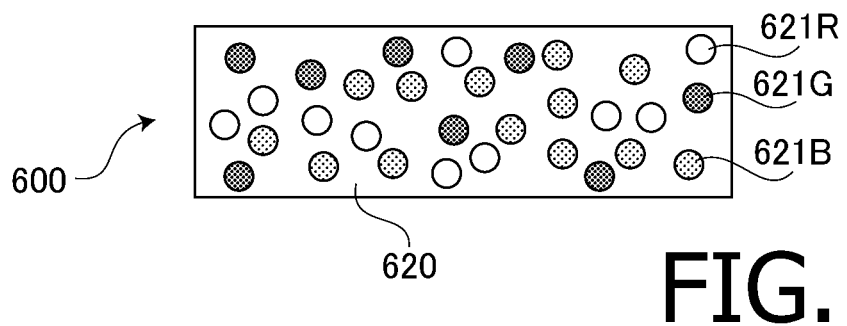
FIG. 17 is a cross-section view of an optical device in the illustrative embodiment according to aspects of the present disclosure.

The optical device 600 may be manufactured by mixing a stain with a transparent material. FIG. 17 shows a cross-section view of the optical device 600 with which a stain is mixed. A transparent material 620 is a material through which light of a visible light band transmits without attenuating substantially, and for example, resin such as polycarbonate or PMMA may be used. Three types of stains 621R, 621G and 621B are mixed with the transparent material 620. The stain 621R changes an intensity of red light transmitted through the optical device 600. The stain 621G changes an intensity of green light transmitted through the optical device 600. The stain 621B changes an intensity of blue light transmitted through the optical device 600. A mixing volume and a mixing ratio of each of the stains 621R, 621G and 621B are determined such that the transmittance of light satisfies formula 10. The transparent material 620 with which the stains 621R, 621G and 621B are mixed are formed into, for example, a shape of eyeglasses or a contact lens. The transparent material 620 may be formed by, for example, a 3D printer or injection molding using a metallic mold.

By the manufacturing method of the optical device 600, the optical device 600 may be manufactured only by mixing the stains 621R, 621G and 621B with the transparent material. Therefore, the method has a merit that it is easy to manufacture the optical device 600.

The manufactured optical device 600 is worn by the subject 300 as eyeglasses or a contact lens. By adjusting a light intensity of color components in light entering into eyes of the subject 300, the color vision characteristics of the subject 300 are adjusted.

What is claimed is:

1. A method for manufacturing an optical device, comprising:

obtaining a plurality of test images in each of which only one of a spectral intensity of a first color component, a spectral intensity of a second color component, and a spectral intensity of a third color component is changeable, and other color components are fixed, a wavelength of the second color component being shorter than a wavelength of the first color component, a wavelength of the third color component being shorter than the wavelength of the second color component, the plurality of test images including a first test image and a second test image, the first test image and the second test image having respective different colors of which the spectral intensities are changeable, only the spectral intensity of the first color component being changeable in the first test image, only the spectral intensity of the second color component being changeable in the second test image;

changing the spectral intensity of the first color component in the first test image without changing the spectral intensity of the second color component and without changing the spectral intensity of the third color component in the first test image in a state where a subject is looking at not the second test image but only the first test image;

obtaining a spectral intensity Rs of the first color component in the first test image, the spectral intensity Rs satisfying a first particular test condition when the subject is looking at the first test image in which the spectral intensity of the first color component is being changed;

changing the spectral intensity of the second color component in the second test image without changing the spectral intensity of the first color component and without changing the spectral intensity of the third color component in the second test image in a state where the subject is looking at not the first test image but only the second test image;

obtaining a spectral intensity Gs of the second color component in the second test image, the spectral intensity Gs satisfying a second particular test condition when the subject is looking at the second test image in which the spectral intensity of the second color component is being changed; and manufacturing the optical device including an optical element configured to adjust a light intensity of the first color component and a light intensity of the second color component, in light transmitted through the optical element, based on the spectral intensity Rs and the spectral intensity Gs.

2. The method for manufacturing the optical device according to claim 1, wherein the plurality of test images includes:
   a third test image in which a spectral intensity of the second color component and a spectral intensity of the third color component are equal to the spectral intensity of the second color component and the spectral intensity of the third color component in the first test image, respectively; and
   a fourth test image in which a spectral intensity of the first color component and a spectral intensity of the third color component are equal to the spectral intensity of the first color component and the spectral intensity of the third color component in the second test image, respectively, and wherein the particular test condition includes:
   a condition that a color difference between the first test image and the third test image is changed from a state unrecognizable to the subject to a state recognizable to the subject when the spectral intensity of the first color component in the first test image is changed from a value equal to the spectral intensity of the first color component in the third test image; and
   a condition that a color difference between the second test image and the fourth test image is changed from a state unrecognizable to the subject to a state recognizable to the subject when the spectral intensity of the second color component in the second test image is changed from a value equal to the spectral intensity of the second color component in the fourth test image.

3. The method for manufacturing the optical device according to claim 2, wherein the spectral intensity of the first color component, the spectral intensity of the second color component and the spectral intensity of the third color component of the third test image are changeable, wherein, among the first color component, the second color component and the third color component of the first test image, only the spectral intensity of the first color component of the first test image is changeable from a state where the first test image and the third test image have a same color, wherein the spectral intensity of the first color component, the spectral intensity of the second color component and the spectral intensity of the third color component of the fourth test image are changeable, and wherein, among the first color component, the second color component and the third color component of the second test image, only the spectral intensity of the second color component of the second test image is changeable from a state where the second test image and the fourth test image have a same color.

4. The method for manufacturing the optical device according to claim 2, wherein the optical element is further configured to:
   adjust the light intensity of the first color component in the transmitted light to be multiplied by a value of particular times as large as a change amount, satisfying the particular test condition, of the spectral intensity of the first color component in the first test image; and
   adjust the light intensity of the second color component in the transmitted light to be multiplied by a value of the particular times as large as a change amount, satisfying the particular test condition, of the spectral intensity of the second color component in the second test image.

5. The method for manufacturing the optical device according to claim 1, further comprising:
   obtaining a first comparison image and a second comparison image having respective colors different from each other and having a same spectral intensity of the third color component;
   simultaneously changing a spectral intensity of the third color component in the first comparison image and a spectral intensity of the third color component in the second comparison image; and
   obtaining spectral intensities Bm of the third color components in the first comparison image and the second comparison image, the spectral intensities Bm satisfying a particular comparison condition when the subject is looking at the first and second comparison images, wherein the optical device is manufactured further including an optical element for third color component that is configured to adjust a light intensity of the third color component in the transmitted light based on the spectral intensity Bm.

6. The method for manufacturing the optical device according to claim 5, further comprising obtaining a maximum value Bmax of the spectral intensities of the third color components in the first comparison image and the second comparison image, wherein the optical element for the third color component is further configured to adjust the light intensity of the third color component in the transmitted light to be multiplied by Bm/Bmax.

7. The method for manufacturing the optical device according to claim 5, wherein the particular comparison condition is such a condition as to achieve a highest visibility for the subject to visually recognize a color difference between the first comparison image and the second comparison image.

8. The method for manufacturing the optical device according to claim 5, further comprising:
   fixing the spectral intensity of the third color component in the first comparison image and the spectral intensity of the third color component in the second comparison image to the spectral intensity Bm, and changing a spectral intensity of the first color component in the first comparison image and a spectral intensity of the second color component in the second comparison image in such a manner that the two spectral intensities are equal to each other; and
   obtaining a spectral intensity Rc of the first color component in the first comparison image and a spectral intensity Gc of the second color component in the second comparison image, the spectral intensity Rc and the spectral intensity Gc satisfying the particular comparison condition when the subject is looking at the first comparison image and the second comparison image, wherein the optical element is further configured to adjust the light intensity of the first color component and the light intensity of the second color component in the transmitted light based on at least one of the spectral intensity Rc and the spectral intensity Gc.

9. An optical device comprising:

an optical element configured to adjust a light intensity of a first color component and a light intensity of a second color component in light transmitted through the optical element, based on a spectral intensity Rs and a spectral intensity Gs, a wavelength of the second color component being shorter than a wavelength of the first color component, wherein the spectral intensity Rs and the spectral intensity Gs are determined by:

obtaining a plurality of test images in each of which only one of a spectral intensity of the first color component, a spectral intensity of the second color component, and a spectral intensity of a third color component is changeable, and other color components are fixed, a wavelength of the third color component being shorter than the wavelength of the second color component, the plurality of test images including a first test image and a second test image, the first test image and the second test image having respective different colors of which the spectral intensities are changeable, only the spectral intensity of the first color component being changeable in the first test image, only the spectral intensity of the second color component being changeable in the second test image;

changing the spectral intensity of the first color component in the first test image without changing the spectral intensity of the second color component and without changing the spectral intensity of the third color component in the first test image in a state where a subject is looking at not the second test image but only the first test image;

obtaining a spectral intensity Rs of the first color component in the first test image, the spectral intensity Rs satisfying a first particular test condition when the subject is looking at the first test image in which the spectral intensity of the first color component is being changed;

changing the spectral intensity of the second color component in the second test image without changing the spectral intensity of the first color component and without changing the spectral intensity of the third color component in the second test image in a state where the subject is looking at not the first test image but only the second test image; and obtaining a spectral intensity Gs of the second color component in the second test image, the spectral intensity Gs satisfying a second particular test condition when the subject is looking at the second test image in which the spectral intensity of the second color component is being changed.

10. The optical device according to claim 9, wherein the plurality of test images includes:

a third test image in which a spectral intensity of the second color component and a spectral intensity of the third color component are equal to the spectral intensity of the second color component and the spectral intensity of the third color component in the first test image, respectively; and a fourth test image in which a spectral intensity of the first color component and a spectral intensity of the third color component are equal to the spectral intensity of the first color component and the spectral intensity of the third color component in the first test image, respectively, and wherein the particular test condition includes:

a condition that a color difference between the first test image and the third test image is changed from a state unrecognizable to the subject to a state recognizable to the subject when the spectral intensity of the first color component in the first test image is changed from a value equal to the spectral intensity of the first color component in the third test image; and a condition that a color difference between the second test image and the fourth test image is changed from a state unrecognizable to the subject to a state recognizable to the subject when the spectral intensity of the second color component in the second test image is changed from a value equal to the spectral intensity of the second color component in the fourth test image.

11. The optical device according to claim 10, wherein the spectral intensity of the first color component, the spectral intensity of the second color component and the spectral intensity of the third color component of the third test image are changeable, wherein, among the first color component, the second color component and the third color component of the first test image, only the spectral intensity of the first color component of the first test image is changeable from a state where the first test image and the third test image have a same color, wherein the spectral intensity of the first color component, the spectral intensity of the second color component and the spectral intensity of the third color component of the fourth test image are changeable, and wherein, among the first color component, the second color component and the third color component of the second test image, only the spectral intensity of the second color component of the second test image is changeable from a state where the second test image and the fourth test image have a same color.

12. The optical device according to claim 10, wherein the optical element is further configured to:

adjust the light intensity of the first color component in the transmitted to be multiplied by a value of particular times as large as a change amount, satisfying the particular test condition, of the spectral intensity of the first color component in the first test image; and adjust the light intensity of the second color component in the transmitted light to be multiplied by a value of the particular times as large as a change amount, satisfying the particular test condition, of the spectral intensity of the second color component in the second test image.

13. The optical device according to claim 9, further comprising an optical element for the third color component configured to adjust a light intensity of the third color component transmitted through the optical element for the third color component, based on a spectral intensity Bm, wherein the spectral intensity Bm is determined by:
obtaining a first comparison image and a second comparison image having respective colors different from each other and having a same spectral intensity of the third color component;
simultaneously changing a spectral intensity of the third color component in the first comparison image and a spectral intensity of the third color component in the second comparison image; and
obtaining the spectral intensities Bm of the third color components in the first comparison image and the second comparison image satisfying a particular comparison condition when the subject is looking at the first and second comparison images is spectral intensity Bm.

14. The optical device according to claim 13,
wherein, when a maximum value of the spectral intensities of the third color component in the first comparison image and the second comparison image are spectral intensity Bmax, the optical element for the third color component adjusts the light intensity of the third color component in the transmitted light to be multiplied by Bm/Bmax.

15. The optical device according to claim 13,
wherein the particular comparison condition is such a condition as to achieve a highest visibility for the subject to visually recognize a color difference between the first comparison image and the second comparison image.

16. The optical device according to claim 13,
wherein the optical device is further configured to adjust the light intensity of the first color component and the light intensity of the second color component in the transmitted light based on at least one of a spectral intensity Rc and a spectral intensity Gc:
wherein the spectral intensity Rc and the spectral intensity Gc are determined by:
fixing the spectral intensity of the third color component in the first comparison image and the spectral intensity of the third color component in the second comparison image to the spectral intensity Bm, and changing a spectral intensity of the first color component in the first comparison image and a spectral intensity of the second color component in the second comparison image in such a manner that the two spectral intensities are equal to each other; and
obtaining the spectral intensity Rc of the first color component in the first comparison image and the spectral intensity Gc of the second color component in the second comparison image, which satisfy the particular comparison condition when the subject is looking at the first comparison image and the second comparison image.

17. A non-transitory computer-readable storage medium storing computer-readable instructions configured to, when executed by a computer, cause the computer to execute functions comprising:
obtain a plurality of test images in each of which only one of a spectral intensity of a first color component, a spectral intensity of a second color component, and a spectral intensity of a third color component is changeable, and other color components are fixed, a wavelength of the second color component being shorter than a wavelength of the first color component, a wavelength of the third color component being shorter than the wavelength of the second color component, the plurality of test images including a first test image and a second test image, the first test image and the second test image having respective different colors of which the spectral intensities are changeable, only the spectral intensity of the first color component being changeable in the first test image, only the spectral intensity of the second color component being changeable in the second test image;
change the spectral intensity of the first color component in the first test image without changing the spectral intensity of the second color component and without changing the spectral intensity of the third color component in the first test image in a state where a subject is looking at not the second test image but only the first test image;
obtain a spectral intensity Rs of the first color component in the first test image, the spectral intensity Rs satisfying a first particular test condition when the subject is looking at the first test image in which the spectral intensity of the first color component is being changed;
change the spectral intensity of the second color component in the second test image without changing the spectral intensity of the first color component and without changing the spectral intensity of the third color component in the second test image in a state where the subject is looking at not the first test image but only the second test image;
obtain a spectral intensity Gs of the second color component in the second test image, the spectral intensity Gs satisfying a second particular test condition when the subject is looking at the second test image in which the spectral intensity of the second color component is being changed;
display an image based on an image signal; and
adjust at least one of a spectral intensity of the first color component and a spectral intensity of the second color component, in the image based on the image signal, based on the spectral intensity Rs and the spectral intensity Gs.

18. The non-transitory computer-readable storage medium according to claim 17,
wherein the plurality of test images includes:
a third test image in which spectral intensity of the second color component and spectral intensity of the third color component are equal to the spectral intensity of the second color component and the spectral intensity of the third color component in the first test image, respectively; and
a fourth test image in which spectral intensity of the first color component and spectral intensity of the third color component are equal to the spectral intensity of the first color component and the spectral intensity of the third color component in the first test image, respectively; and
wherein the particular test condition includes:
a condition that a color difference between the first test image and the third test image is changed from a state unrecognizable to the subject to a state recognizable to the subject when the spectral intensity of the first color component in the first test image is changed from a value equal to the spectral intensity of the first color component in the third test image; and
a condition that a color difference between the second test image and the fourth test image is changed from a state unrecognizable to the subject to a state recognizable to the subject when the spectral intensity of the second color component in the second test image is changed from a value equal to the spectral intensity of the second color component in the fourth test image.

19. The non-transitory computer-readable storage medium according to claim 18,
wherein the spectral intensity of the first color component, the spectral intensity of the second color component and the spectral intensity of the third color component of the third test image are changeable,
wherein, among the first color component, the second color component and the third color component of the first test image, only the spectral intensity of the first color component of the first test image is changeable from a state where the first test image and the third test image have a same color,
wherein the spectral intensity of the first color component, the spectral intensity of the second color component and the spectral intensity of the third color component of the fourth test image are changeable, and
wherein, among the first color component, the second color component and the third color component of the second test image, only the spectral intensity of the second color component of the second test image is changeable from a state where the second test image and the fourth test image have a same color.

20. The non-transitory computer-readable storage medium according to claim 18,
wherein the instructions, when executed, further cause the computer to:
adjust the spectral intensity of the first color component in the image to be multiplied by a value of particular times as large as a change amount, satisfying the particular test condition, of the spectral intensity of the first color component of the first test image; and
adjust the spectral intensity of the second color component in the image to be multiplied by a value of the particular times as large as a change amount, satisfying the particular test condition, of the spectral intensity of the second color component of the second test image.

21. The non-transitory computer-readable storage medium according to claim 17,
wherein the instructions, when executed, further cause the computer to:
obtain a first comparison image and a second comparison image having respective colors different from each other and having a same spectral intensity of the third color component;
simultaneously change a spectral intensity of the third color component in the first comparison image and a spectral intensity of the third color component in the second comparison image;
obtain spectral intensities Bm of the third color components in the first comparison image and the second comparison image, the spectral intensities Bm satisfying a particular comparison condition when the subject is looking at the first and second comparison images; and
adjust a spectral intensity of the third color component, in the image based on the image signal, based on the spectral intensity Bm.

22. The non-transitory computer-readable storage medium according to claim 21,
wherein the instructions, when executed, further cause the computer to:
obtain a maximum value Bmax of the spectral intensities of the third color components in the first comparison image and the second comparison image; and
adjust the spectral intensity of the third color component in the image to be multiplied by Bm/Bmax.

23. The non-transitory computer-readable storage medium according to claim 21,
wherein the particular comparison condition is such a condition as to achieve a highest visibility for the subject to visually recognize a color difference between the first comparison image and the second comparison image.

24. The non-transitory computer-readable storage medium according to claim 21,
wherein the instructions, when executed, further cause the computer to:
fix the spectral intensity of the third color component in the first comparison image and the spectral intensity of the third color component in the second comparison image to the spectral intensity Bm, and changing a spectral intensity of the first color component in the first comparison image and a spectral intensity of the second color component in the second comparison image in such a manner that the two spectral intensities are equal to each other;
obtain a spectral intensity Rc of the first color component in the first comparison image and a spectral intensity Gc of the second color component in the second comparison image, the spectral intensity Rc and the spectral intensity Gc satisfying the particular comparison condition when the subject is looking at the first comparison image and the second comparison image; and
adjust the spectral intensity of the first color component and the spectral intensity of the second color component in the image based on at least one of the spectral intensity Rc and the spectral intensity Gc.

25. A color adjusting device, comprising:
a test image setter configured to obtain a plurality of test images in each of which only one of a spectral intensity of a first color component, a spectral intensity of a second color component, and a spectral intensity of a third color component is changeable, and other color components are fixed, a wavelength of the second color component being shorter than a wavelength of the first color component, a wavelength of the third color component being shorter than the wavelength of the second color component, the plurality of test images including a first test image and a second test image, the first test image and the second test image having respective different colors of which the spectral intensities are changeable, only the spectral intensity of the first color component being changeable in the first test image, only the spectral intensity of the second color component being changeable in the second test image;
a spectral intensity changer configured to:
change the spectral intensity of the first color component in the first test image without changing the spectral intensity of the second color component and without changing the spectral intensity of the third color component in the first test image in a state where a subject is looking at not the second test image but only the first test image; and change the spectral intensity of the second color component in the second test image without changing the spectral intensity of the first color component and without changing the spectral intensity of the third color component in the second test image in a state where the subject is looking at not the first test image but only the second test image;

a spectral intensity obtainer configured to:
  obtain a spectral intensity Rs of the first color component in the first test image, the spectral intensity Rs satisfying a first particular test condition when the subject is looking at the first test image in which the spectral intensity of the first color component is being changed; and
  obtain a spectral intensity Gs of the second color component in the second test image, the spectral intensity Gs satisfying a second particular test condition when the subject is looking at the second test image in which the spectral intensity of the second color component is being changed;

an image displayer configured to display an image based on an image signal; and a spectral intensity adjuster configured to adjust at least one of a spectral intensity of the first color component and a spectral intensity of the second color component, in the image based on the image signal, based on the spectral intensity Rs and the spectral intensity Gs.

26. The color adjusting device according to claim 25, wherein the plurality of test images includes:
  a third test image in which spectral intensity of the second color component and spectral intensity of the third color component are equal to the spectral intensity of the second color component and the spectral intensity of the third color component in the first test image, respectively; and
  a fourth test image in which spectral intensity of the first color component and spectral intensity of the third color component are equal to the spectral intensity of the first color component and the spectral intensity of the third color component in the first test image, respectively; and
wherein the particular test condition includes:
  a condition that a color difference between the first test image and the third test image is changed from a state unrecognizable to the subject to a state recognizable to the subject when the spectral intensity of the first color component in the first test image is changed from a value equal to the spectral intensity of the first color component in the third test image; and
  a condition that a color difference between the second test image and the fourth test image is changed from a state unrecognizable to the subject to a state recognizable to the subject when the spectral intensity of the second color component in the second test image is changed from a value equal to the spectral intensity of the second color component in the fourth test image.

27. The color adjusting device according to claim 26, wherein the spectral intensity of the first color component, the spectral intensity of the second color component and the spectral intensity of the third color component of the third test image are changeable,
wherein, among the first color component, the second color component and the third color component of the first test image, only the spectral intensity of the first color component of the first test image is changeable from a state where the first test image and the third test image have a same color,
wherein the spectral intensity of the first color component, the spectral intensity of the second color component and the spectral intensity of the third color component of the fourth test image are changeable, and
wherein, among the first color component, the second color component and the third color component of the second test image, only the spectral intensity of the second color component of the second test image is changeable from a state where the second test image and the fourth test image have a same color.

28. The color adjusting device according to claim 26, wherein the spectral intensity adjuster is configured to:
  adjust the spectral intensity of the first color component in the image to be multiplied by a value of particular times as large as a change amount, satisfying the particular test condition, of the spectral intensity of the first color component of the first test image; and
  adjust the spectral intensity of the second color component in the image to be multiplied by a value of the particular times as large as a change amount, satisfying the particular test condition, of the spectral intensity of the second color component of the second test image.

29. The color adjusting device according to claim 25, further comprising a comparison image setter configured to set a first comparison image and a second comparison image having respective colors different from each other and having a same value of the third color component,
wherein the spectral intensity changer simultaneously changes a spectral intensity of the third color component in the first comparison image and a spectral intensity of the third color component in the second comparison image,
wherein the spectral intensity obtainer obtains spectral intensity Bm of the third color components in the first comparison image and the second comparison image, the spectral intensity Bm satisfying a particular comparison condition when the subject is looking at the first and second comparison images;
wherein the spectral intensity adjuster adjusts a spectral intensity of the third color component, in the image based on the image signal, based on the spectral intensity Bm.

30. The color adjusting device according to claim 29, further comprising a maximum value obtainer configure to obtain a maximum value Bmax of the spectral intensity of the third color components in the first comparison image and the second comparison image,
  wherein the spectral intensity adjuster adjusts the spectral intensity of the third color component in the image to be multiplied by Bm/Bmax.

31. The color adjusting device according to claim 29, wherein the particular comparison condition is such a condition as to achieve a highest visibility for the subject to visually recognize a color difference between the first comparison image and the second comparison image.

32. The color adjusting device according to claim 29, wherein the spectral intensity adjuster fixes the spectral intensity of the third color component in the first comparison image and the spectral intensity of the third color component in the second comparison image to the spectral intensity Bm, and changes a spectral intensity of the first color component in the first comparison image and a spectral intensity of the second color component in the second comparison image in such a manner that the two spectral intensities are equal to each other, wherein the spectral intensity obtainer obtains a spectral intensity Rc of the first color component in the first comparison image and a spectral intensity Gc of the second color component in the second comparison image, the spectral intensity Rc and the spectral intensity Gc satisfying the particular comparison condition when the subject is looking at the first comparison image and the second comparison image, and wherein the spectral intensity adjuster adjusts the spectral intensity of the first color component and the spectral intensity of the second color component in the image based on at least one of the spectral intensity Rc and the spectral intensity Gc.

\* \* \* \* \*